US007629444B1

(12) United States Patent
Goldman et al.

(10) Patent No.: US 7,629,444 B1
(45) Date of Patent: Dec. 8, 2009

(54) **NUCLEOTIDE AND AMINO ACID SEQUENCES FROM *XENORHABDUS BOVIENII* STRAIN XS85831 AND USES THEREOF**

(75) Inventors: Barry S. Goldman, St. Louis, MO (US); Karina Krasomil-Osterfeld, Ellisville, MO (US); Wei Wu, St. Louis, MO (US)

(73) Assignee: Monsanto Technology LLC, St. Louis, MO (US)

( * ) Notice: Subject to any disclaimer, the term of this patent is extended or adjusted under 35 U.S.C. 154(b) by 0 days.

(21) Appl. No.: 11/150,804

(22) Filed: Jun. 10, 2005

Related U.S. Application Data

(60) Provisional application No. 60/579,902, filed on Jun. 15, 2004.

(51) Int. Cl.
*C07H 21/02* (2006.01)
*C07H 21/04* (2006.01)
(52) U.S. Cl. .................... 536/23.1; 536/23.7
(58) Field of Classification Search .............. None
See application file for complete search history.

(56) References Cited

U.S. PATENT DOCUMENTS 7,285,632 B2    10/2007    Apel-Birkhold et al.

OTHER PUBLICATIONS

Ngo et al., in The Protein Folding Problem and Tertiary Structure Prediction, 1994, Merz et al. (ed.), Birkhauser, Boston, MA, pp. 433 and 492-495.*
Branden et al. (Introduction to Protein Structure, Garland Publishing Inc., New York, p. 247).*
Witkowski et al., Biochemistry, 38, 11643-11650, 1999.*
Wishart et al., Journal of Biological Chemistry, vol. 270, No. 45, pp. 26782-26785, 1995.*
Kisselev, Structure, vol. 10, pp. 8-9, 2002.*
NCBI Website, BLASTP Accession No. AAC38625 dated Jun. 30, 1998.
NCBI Website, BLASTP Accession No. NP928295 dated May 1, 2009.
NCBI Website, BLASTP Accession No. AAL18483 dated Jul. 17, 2003.
NCBI Website, BLASTP Accession No. ABG33866 dated Oct. 21, 2008.
NCBI Website, BLASTP Accession No. AAL18451 dated Oct. 25, 2001.
NCBI Website, BLASTP Accession No. ABB43160 dated Nov. 5, 2005.
NCBI Website, BLASTP Accession No. NP927868 dated May 1, 2009.
NCBI Website, BLASTP Accession No. CAE12810 dated Apr. 17, 2005.
NCBI Website, BLASTP Accession No. CAE13256 dated Apr. 17, 2005.
NCBI Website, BLASTP Accession No. YP002026051 dated Aug. 5, 2008.
NCBI Website, BLASTP Accession No. YP335902 dated Apr. 30, 2009.
NCBI Website, BLASTP Accession No. ABA52036 dated Sep. 30, 2005.
NCBI Website, BLASTP Accession No. EDO95309 dated Oct. 9, 2007.

\* cited by examiner

*Primary Examiner*—Suzanne M. Noakes
*Assistant Examiner*—Jae W Lee
(74) *Attorney, Agent, or Firm*—Timothy K. Ball; Arnold & Porter LLP

(57) ABSTRACT

The present invention relates to nucleic acid sequences from *Xenorhabdus*, and, in particular, to genomic DNA sequences, and to nucleotide sequences that encode insecticidal proteins from *Xenorhabdus bovienii*, strain Xs85831. The invention encompasses nucleic acid molecules present in non-coding regions as well as nucleic acid molecules that encode proteins, fragments of proteins, tRNA's, fragments of tRNA's, rRNA's, and fragments of rRNA's. In addition, proteins and fragments thereof and antibodies capable of binding specifically to the proteins are encompassed by the present invention. The invention also relates to methods of using the disclosed nucleic acid molecules, proteins, protein fragments, RNA's, and antibodies, for example, for gene identification and analysis, preparation of constructs, and protecting plants from insect infestations.

6 Claims, No Drawings

US 7,629,444 B1

NUCLEOTIDE AND AMINO ACID SEQUENCES FROM *XENORHABDUS BOVIENII* STRAIN XS85831 AND USES THEREOF

CROSS REFERENCE TO RELATED APPLICATIONS

This application claims the benefit of priority to U.S. Provisional Application Ser. No. 60/579,902, filed Jun. 15, 2004, which is incorporated herein by reference in its entirety.

BACKGROUND OF THE INVENTION

1. Field of the Invention

The present invention discloses nucleic acid sequences from *Xenorhabdus bovienii*, methods of using the disclosed nucleic acid sequences to encode proteins and fragments of proteins, antibodies exhibiting binding specificity for the encoded proteins, transformation of cells such as bacterial cells and plant cells with the nucleic acid sequences or derivatives thereof to produce useful *Xenorhabdus* proteins or fragments thereof, including but not limited to insecticidal, bactericidal, fungicidal, nematicidal, antibiotic resistance, and polyketide proteins, and the like.

2. Background of the Invention

*Xenorhabdus* species are Gram-negative bacteria, members of the family Enterobacteriaceae, and symbiotically associated with nematodes species of the genus *Steinernema*. The nematode-bacterial complex can be characterized as an obligate parasitic relationship, specializing in parasitizing and proliferating in soil insect larvae. Infective, non-feeding stages of these nematodes live in soil and carry in their gut the nematode-genus-specific symbiotic strain of *Xenorhabdus* bacteria. It is believed that the nematodes actively search for the appropriate insect host, invade the insect larvae through natural openings or lesions in the cuticle and, once inside the hemolymph, release their symbiotic bacteria. The nematode-bacterial complex secretes a variety of highly efficient extracellular metabolites and proteins exhibiting insecticidal, bactericidal, fungicidal and nematocidal properties that secures the larval mass as a source of nutrition. An array of extracellular enzymes such as lipases, phospholipases, proteases, and nucleases as well as several broad spectrum antibiotics, and antifungal and nematocidal compositions are also secreted (Boemare & Akhurst, J. Gen. Microbiol. 134: 751-761, 1988; Li et al., Can. J. Microbiol. 43(8):770-773, 1997; McInerney et al., J. Nat. Prod. 54(3):774-84, 1991; McInerney et al., J. Nat. Prod. 54(3):785-95, 1991; Sundar and Chang, J. Gen. Microbiol. 139 (Pt 12):3139-48, 1993). It has been discovered that some compounds secreted by *Xenorhabdus* exhibit anti-neoplastic (U.S. Pat. No. 5,827,872), acaricidal, anti-inflammatory and anti-ulcerogenic properties (U.S. Pat. No. 4,837,222). U.S. Pat. No. 6,048,838 describes insect inhibitory proteins that exhibit a molecular weight of greater than 100 kDa produced by *Xenorhabdus* sp., which are active against a variety of insect species including the orders, Lepidoptera, Coleoptera, Diptera, and Acarina, when provided in an insect diet.

*Xenorhabdus* strains have been shown to produce an array of extracellular proteins and small molecules or secondary metabolites exhibiting specialized functions (Li et al., Can. J. Microbiol. 43(8):770-773, 1997; McInerney et al., J. Nat. Prod. 54(3):774-84, 1991; U.S. Pat. No. 6,048,838), as well as proteins and small molecules that are more commercially interesting because they exhibit antibiotic properties or insect inhibitory activity. A small number of insect inhibitory proteins have previously been identified from these bacteria, symbionts of insect-parasitic nematodes (Morgan et al., Appl. Environ. Microbiol., 67(5):2062-2069, 2001; U.S. Pat. No. 6,048,838). Such proteins and compositions are used as biologically safe and effective pest control agents. Unlike chemical pesticide compositions, these proteins appear to have no effect upon the environment in general, can be targeted to direct their effect primarily upon target insect species, and have no effect on non-target species. A resistance management strategy that takes advantage of insect inhibitory proteins derived from distinct microbial sources other than *B. thuringiensis* would be desirable. Insect inhibitory proteins isolated from *Xenorhabdus* bacteria exhibit all the prerequisites for the delivery of novel genes for transgenic expression of insect pest inhibitory proteins in plants to provide pest resistance, expressed either alone or in combination with other insecticidal proteins such as Cry proteins from *Bacillus thuringiensis.*

Therefore, there is a great deal of interest in identifying genes that encode new insect inhibiting proteins, as well as other types of proteins produced by *Xenorhabdus* bacteria, such as proteins involved in the synthesis of novel antibiotics, polyketide synthases, lipases, proteases, nucleases, chitinases, restriction endonucleases, transposons, transposases, excisases, endonucleases, as well as other useful proteins and the like. Isolation and sequencing of the entire genome of *Xenorhabdus* has allowed for the dissection and analysis of the genome into discrete genes encoding proteins exhibiting beneficial properties as described herein.

SUMMARY OF THE INVENTION

The present invention provides an isolated *Xenorhabdus bovienii* strain Xs85831 deposited on Jun. 28, 2000 with the Agriculture Research Culture Collection (NRRL) International Depository Authority at 1815 North University Street, in Peoria, Ill. 61604 U.S.A., according to the Budapest Treaty on the International Recognition of the Deposit of Microorganisms for the Purpose of Patent Procedures and was designated as NRRL-30311. The present disclosure illustrates that this strain exhibits insecticidal activity against commercially important insect species including, e.g., those in the orders Coleoptera [e.g., western corn rootworm WCR, southern corn rootworm SCR, northern corn rootworm NCR, Mexican corn rootworm MCR, brazilian corn rootworm BCR (i.e., *Diabrotica* species) and Lepidoptera [e.g., tobacco budworm (TBW, *Heliothis virescens* Fabricius), cotton bollworm (CBW, *Heliothis zea* Boddie), corn earworm (CEW, *Helicoverpa zea* Boddie), beet armyworm (BAW, *Spodotera exigua* Hübner) and black cutworm (BCW, *Agrotis ipsylon* Hufnagel)]. The strain may also exhibit insecticidal activity against other insects including, e.g., Dipteran, Hemipteran and Hymenopteran insects, or sucking and piercing insects. This strain may be used as a source for DNA sequences encoding insecticidal proteins, and when formulated into a composition of matter as a spray, powder or emulsion, for the treatment of plants or animals to inhibit insect infestation.

The present invention provides isolated and purified nucleic acid molecules isolated from *X. bovienii*, strain Xs85831, selected from the group consisting of SEQ ID NO: 1 through SEQ ID NO:5313 and the complements thereof. These nucleic acid molecules are predicted to encode the polypeptides and amino acid sequences selected from the group consisting of SEQ ID NO:5314 to SEQ ID NO:10626. For clarity, the open reading frame (ORF) set forth in SEQ ID NO:1 encodes an amino acid sequence as set forth in SEQ ID NO:5314; the ORF set forth in SEQ ID NO:2 encodes an amino acid sequence as set forth in SEQ ID NO:5315; and this iteration is continuous with respect to the SEQ ID NO's 1-5313, each respective SEQ ID NO representing a separate and distinct ORF corresponding to the next sequential predicted amino acid sequence as set forth in SEQ ID NO:5314-10626, wherein the ORF as set forth in SEQ ID NO:5313 corresponds to the amino acid sequence as set forth in SEQ ID NO:10626.

The invention further provides a method for isolating a nucleic acid molecule comprising a nucleotide sequence encoding a polypeptide or protein the amino acid sequence of which is at least about 70%, 71, 72, 73, 74, 75, 76, 77, 78, 7, 80, 81, 82, 83, 84, 85, 86, 87, 88, 89, 90, 91, 92, 93, 94, 95, 96, 97, 98, 99, or even about 100% identical to a polypeptide selected from the group consisting of SEQ ID NO:5314 to SEQ ID NO:10626. The method comprises obtaining a nucleic acid encoding all or a substantial portion of an amino acid sequence of a *Xenorhabdus* protein homologue comprising: (a) probing a library with a hybridization probe comprising a nucleotide sequence selected from the group consisting of SEQ ID NO:1 through SEQ ID NO:5313; (b) identifying a DNA segment that hybridizes to the probe; (c) isolating the DNA segment identified in step (b); and (d) sequencing the DNA segment isolated in step (c) wherein the sequenced DNA segment encodes all or a substantial portion of a *Xenorhabdus* protein homologue.

The present invention also provides a substantially purified polypeptide or protein comprising an amino acid sequence selected from the group consisting of SEQ ID NO:5314 to SEQ ID NO:10626. In a preferred embodiment, the amino acid sequence is at least about 70% 70%, 71, 72, 73, 74, 75, 76, 77, 78, 7, 80, 81, 82, 83, 84, 85, 86, 87, 88, 89, 90, 91, 92, 93, 94, 95, 96, 97, 98, 99, or even about 100% identical to a polypeptide selected from the group consisting of SEQ ID NO:5314 to SEQ ID NO:10626.

The present invention also provides in the sequence listing a selected group of sequences that exhibit properties of bacterial promoter sequences (SEQ ID NO:10627-SEQ ID NO:13014), sequences that exhibit properties of bacterial termination sequences (SEQ ID NO:13015-SEQ ID NO:14450), and sequences that exhibit homology or identity to bacterial tRNA coding sequences (SEQ ID NO:14451-14541). Contiguous sequences have been assembled from overlapping sequences that contain any or all of the above mentioned SEQ ID NO's and are set forth herein as contigs in the sequence listing form SEQ ID NO:14542 through SEQ ID NO:14985.

The present invention also provides for recombinant expression constructs comprising: (1) a promoter, which functions in a host cell to cause the production of a mRNA molecule; which is operably linked to (2) a structural nucleotide sequence encoding an insecticidal protein selected from the group consisting of SEQ ID NO: 7316, 9584, 9585, 9639 and 9679; which is operably linked to (3) a 3' sequence that functions in said cell to cause termination of transcription.

The present invention also provides a recombinant construct comprising: (1) a promoter, which functions in a host cell to cause the production of a mRNA molecule; which is operably linked to (2) a structural nucleotide sequence selected from the group consisting of SEQ ID NO:1 to SEQ ID NO:5313; which is operably linked to (3) a 3' non-translated sequence that functions in said cell to cause termination of transcription.

The present invention provides a recombinant construct comprising: (1) a promoter, which functions in a host cell to cause the production of a mRNA molecule; which is operably linked to (2) a structural nucleotide sequence encoding a polypeptide selected from the group consisting of SEQ ID NO:5314 through SEQ ID NO:10626; which is operably linked to (3) a 3' non-translated sequence that functions in said cell to cause termination of transcription.

A transformed cell is provided that expresses a chimeric or heterologous nucleic acid molecule which comprises: (1) a promoter, which functions in said cell to cause the production of a mRNA molecule; which is operably linked to (2) a structural nucleic acid molecule selected from the group consisting of SEQ ID NO: 2003, 4271, 4272, 4326 and 4366; which is operably linked to (3) a 3' sequence that functions in said cell to cause termination of transcription. The structural nucleic acid molecule encodes an insecticidal protein.

A plant cell, a mammalian cell, a bacterial cell, an algal cell, an insect cell and a fungal cell transformed with an isolated nucleic acid molecule of the present invention is provided, wherein the nucleic acid molecule is selected from the group consisting of SEQ ID NO:1 through SEQ ID NO:5313, or SEQ ID NO:14451 through SEQ ID NO:14541, or the complement thereof.

Isolated nucleic acid molecules are provided comprising nucleotide sequences encoding polypeptides or proteins exhibiting insect inhibitory activity, wherein the activity is manifested by inhibiting the growth or development of, or contributing substantially to, or causing the death of a Coleopteran, a Dipteran, a Lepidopteran, a Hemipteran, a Hymenopteran, or a sucking and piercing insect or insect larvae thereof. Also provided are nucleotide sequences encoding novel proteins comprising polypeptides which augment the activity of polypeptides exhibiting insect inhibitory activity when fed to Coleopteran, Dipteran, Lepidopteran, Hemipteran, Hymenopteran, or sucking and piercing insects or insect larvae thereof.

A method for using an insect inhibitory protein isolated from *X. bovienii*, strain Xs85831, is provided. The protein is useful for controlling target insect pests in a plant, wherein the insect inhibitory protein comprises a polypeptide sequence that is selected from the group consisting of SEQ ID NO's: 7316, 9584, 9585, 9639 and 9679. The method comprises the steps of: a) introducing into the genome of the plant an exogenous nucleic acid, wherein the exogenous nucleic acid comprises in the 5' to 3' direction i) a promoter that functions in the cells of said plant, said promoter operably linked to; ii) a structural nucleotide sequence encoding a polypeptide or protein the amino acid sequence of which is substantially identical to a sequence selected from the group consisting of SEQ ID NO's: 7316, 9584, 9585, 9639 and 9679, said structural nucleic acid sequence operably linked to; iii) a 3' non-translated nucleic acid sequence that functions in said cells of said plant to cause transcriptional termination; b) obtaining transformed plant cells containing the nucleic acid sequence of step (a); and c) regenerating from said transformed plant cells a transformed plant in which said polypeptide or protein is overexpressed.

A computer readable medium is provided having recorded thereon one or more of the nucleotide sequences depicted in SEQ ID NO:1 through SEQ ID NO:14985 or with respect to the nucleotide sequences therein, the complements thereof, useful at least as a library of information that can be searched for sequences that are or are substantially identical to the sequences within the library with reference to a query sequence. The computer readable medium can also be used to select sequences for use as probes or primers for identifying and/or detecting in a biological sample the presence of a probe or primer sequence or sequence between primer pairs.

BRIEF DESCRIPTION OF THE SEQUENCES

The sequences disclosed herein have been provided under 37 CFR §1.821-1.825 on CD-ROM diskette. A copy of the Sequence Listing referred to herein is submitted in computer readable form (CRF) on CD-ROM diskette in accordance with the requirements of 37 CFR §1.821(e) and 37CFR §1.52(e) and on two additional diskettes labeled as Copy 1 and Copy 2 respectively. The Sequence Listing in CRF is incorporated herein by reference in its entirety. The contents of the Sequence Listing (CRF) and the two additional CD-ROM diskettes labeled Copy 1 and Copy 2 are the same, and each contains a single 25.023 megabyte text file labeled as Xeno53444_seqListing.txt created with PatentIn version 3.0 software or the equivalent thereof on Jun. 8, 2005, the content of which passed the scrutiny of the USPTO PatentIn Checker software version 1.0.0.1.

Nucleotide sequences from SEQ ID NO:1 to SEQ ID NO:5313 as set forth in the Sequence Listing represent predicted open reading frames encoding peptides that are set forth at SEQ ID NO:5314 to SEQ ID NO:10616. SEQ ID NO:1 represents a predicted ORF, the amino acid sequence translation of which corresponds to the peptide sequence as set forth at SEQ ID NO:5314. Each sequential SEQ ID NO, 2 through 5313, represents a separate predicted ORF, the amino acid sequence of which is set forth at SEQ ID NO:5315-SEQ ID NO:10616. The peptide sequence corresponding to any given nucleotide sequence set forth at SEQ ID NO:1-SEQ ID NO:5313 can be quickly identified by adding 5313 to the number of the SEQ ID NO. For example, the peptide sequence corresponding to the nucleotide sequence ORF as set froth at SEQ ID NO: 201 can be quickly identified by adding 5313 to 201 to arrive at SEQ ID NO:5514. Most SEQ ID NO's corresponding to nucleotide sequences are also identified herein as being present in a contiguous nucleotide sequence representing a large segment of the *Xenorhabdus* genome. The contiguous sequences, individually referred to herein as a CONTIG, or collectively as CONTIGS, are set forth herein as SEQ ID NO:14542-SEQ ID NO:14985. Each nucleotide sequence in the Sequence Listing that corresponds to a position or segment within any CONTIG sequence is associated with that CONTIG by reference to the CONTIG in one or more feature fields <220> and <223> within the SEQ ID NO reference fields. For example, SEQ ID NO:1 contains feature field information that indicates that the coding sequence or nucleotide sequence as set forth in SEQ ID NO:1 is also referred to as "Xb4151_4152.C1.gene1.dna". "Xb4151_4152.C1.gene1.dna" refers in part to the CONTIG, identified as "Xb4151_4152.C1", or SEQ ID NO:14542. SEQ ID NO:1 is descriptive of an ORF from nucleotide position 32-556 as set forth in SEQ ID NO:14542. The ORF as set forth in SEQ ID NO:1 corresponds to the reverse complement of the specified nucleotide segment within SEQ ID NO:14542. Each CONTIG contains multiple coding sequences and multiple genes. The sense or antisense direction of an ORF or other coding sequence is identified in a Feature Field by either a "+" or a "−" illustrating whether the nucleotide sequence specified by a given SEQ ID NO exhibits the same sequence ("+") as that illustrated in the CONTIG sequence or the reverse complement sequence ("−") thereof.

Amino acid sequences predicted to be encoded from the ORF nucleotide sequences contain feature fields that are populated with comments describing the results of BLASTP searches that yielded specific information about the identity or similarity of the predicted amino acid sequence with reference to known amino acid sequences. This information is often referred to as the annotation information for a given amino acid sequence. For many of the amino acid sequences as set forth from SEQ ID NO:5314-SEQ ID NO:10626, similar amino acid sequences or "hits" were readily identifiable using one or more BLASTP search algorithm specified hereinbelow. For those amino acid sequences for which hits were identified, information is provided with respect to the gene classification, the predictive function of the protein, the functional class of the protein family if any that the predicted protein may belong to, the portion of the query sequence (the predicted amino acid sequence as set forth in the SEQ ID NO) that resulted in the identification of the hit, the portion of the hit sequence that resulted in the closest match being established, the BLASTP score, the relative percent identity or similarity, if any, and the database sequence identifier for the hit sequence whether from SWISSPROT, GENBANK, or otherwise, as well as any other information that may be believed to be relevant to identification and classification of the amino acid sequence presented within each SEQ ID NO.

*Xenorhabdus* Xs85831 nucleotide sequences corresponding to predicted bacterial consensus promoter sequences upstream from various ORF's or other genes identified in the instant invention are set forth in the Sequence Listing from SEQ ID NO:10627 through SEQ ID NO:13014. The position of these predicted promoter sequences within any given CONTIG is also specified as indicated above, along with any information about orientation of the promoter with respect to the CONTIG sequence.

Translational termination sequences are relatively simple sequences in bacterial systems, and *Xenorhabdus* Xs85831 termination sequences appear to fall within these consensus identification rules. Such termination sequences are set forth in the Sequence Listing from SEQ ID NO:13015 through SEQ ID NO:14450

Nucleotide sequences corresponding to predicted genes encoding various tRNA homologs from *Xenorhabdus* Xs85831 and their annotations are set forth in the Sequence Listing from SEQ ID NO:14451 through SEQ ID NO:14541.

In summary, the following list is a brief description of the blocks of sequences as set out in the Sequence Listing.

SEQ ID NO:1 through SEQ ID NO:5313 represent predicted open reading frames that have been isolated and characterized from the genome of *X. bovienii*, strain Xs85831.

SEQ ID NO:5314 through SEQ ID NO:10626 represent the predicted amino acid sequence translation of each of the above specified open reading frames.

SEQ ID NO:10627 through SEQ ID NO:13014 represent predicted promoter nucleotide sequences isolated and characterized from the genome of *X. bovienii*, strain Xs85831.

SEQ ID NO:13015 through SEQ ID NO:14450 represent predicted translational termination sequences isolated and characterized from the genome of *X. bovienii*, strain Xs85831.

SEQ ID NO:14451 through SEQ ID NO:14541 represent nucleotide sequences predicted to encode various tRNA and rRNA isolated and characterized from the genome of *X. bovienii*, strain Xs85831.

SEQ ID NO:14542 through SEQ ID NO:14985 represent contiguous sequences of the genome of *X. bovienii*, strain Xs85831 specified herein as CONTIG sequences assembled as a result of overlapping individual nucleotide sequences using bioinformatic methods.

DETAILED DESCRIPTION OF THE INVENTION

In accordance with the present invention, novel nucleic acid molecules have been isolated from a bacterium *Xhenorhabdus. bovienii*, strain Xs85831. Polypeptides or proteins, tRNA and rRNA encoded from the novel nucleotide sequences are also provided. Isolated nucleic acid molecules comprising regulatory elements that include promoter and translational termination sequences are also provided. The present invention provides isolated nucleic acid molecules that encode a class of proteins that exhibit insect inhibitory activity, wherein the activity is manifested by inhibiting the growth or development of, or contributing substantially to, or causing the death of an insect, such as a Coleopteran, a Dipteran, a Lepidopteran, a Hemipteran, a Hymenopteran, or a sucking and piercing insect. Those skilled in the art will find utility of these insecticidal proteins in protecting plants from insect infestations, and in formulations for preventing insect infestations.

In another embodiment, the present invention provides isolated nucleic acid molecules that encode a class of proteins or polypeptides that are useful in providing compositions comprising, e.g., insect inhibitory proteins, microbial inhibitory proteins including bactericidal and fungistatic proteins, nematocidal and protein homologs of chitinases, histones and restriction enzymes, proteases, proteins capable of conferring resistance to heavy metals or other toxic compositions, polyketide synthases, antibiotic, cellular functions, restriction endonucleases, proteases, chitinases, lipases, cellulases, metabolic functions, catabolic functions, anabolic functions, regulatory proteins, transcription and translation proteins, and transposases, among others.

In still another embodiment, the present invention relates to methods of obtaining the disclosed nucleic acid molecules and proteins and of using the disclosed nucleic acid molecules, proteins, fragments of proteins, and antibodies, for example, for gene identification and analysis, preparation of constructs, transformation of cells with nucleotide compositions disclosed herein to produce *Xenorhabdus* proteins or fragments thereof, in particular novel insect inhibitory, bactericidal, fungicidal and nematocidal proteins.

The inventors have identified a strain of *Xenorhabdus* bacteria that exhibits novel insecticidal properties, and based on this observation, have identified the nucleotide sequence of the genomic DNA of the bacterial strain in order to more fully understand the basis of the novel insecticidal properties exhibited by the organism. In identifying the nucleotide sequence of the genome of the bacterium, the inventors identified numerous sequences that overlap at least partially with numerous other sequences, enabling the construction of very large contiguous sequences representing the organizational and structural topology of the genome of the organism, which is then used to compare to other large genomes that have been previously sequenced. In addition, the nucleotide sequences were searched for the presence of various elements, including but not limited to open reading frames (ORF's) encoding proteins, promoter sequences, sequences encoding tRNA and rRNA sequences identified based either on their identity or similarity to other related sequences from other organisms already known in the art, and the like. Such sequences have provided information about how the *Xenorhabdus bovienii* organism of the present invention is able to function in its symbiotic relationship with its commensurate *Steinernema* nematode host, how it is able to fully encompass the biosphere of a target organism in order to establish a pristine environment for the growth and proliferation of its commensurate *Steinernema* nematode host, and information about biological properties that may be useful in medicinal, pharmaceutical, veterinary, and even general household use, as well as enzymes and other molecules that may be useful in diagnostics and research investigations. The following description characterizes a number of the features identified by analysis and characterization of the individual coding sequences of the genome of *Xenorhabdus bovienii* strain Xs85831.

The term "an isolated nucleic acid" refers to a nucleic acid that is no longer accompanied by some of materials with which it is associated in its natural state or to a nucleic acid the structure of which is not identical to that of any of naturally occurring nucleic acid. Examples of an isolated nucleic acid include: (1) DNAs which have the sequence of part of a naturally occurring genomic DNA molecules, but are not flanked by two coding sequences that flank that part of the molecule in the genome of the organism in which it naturally occurs; (2) a nucleic acid incorporated into a vector or into the genomic DNA of a prokaryote or eukaryote in a manner such that the resulting molecule is not identical to any naturally occurring vector or genomic DNA; (3) a separate molecule such as a cDNA, a genomic fragment, a fragment produced by polymerase chain reaction (PCR), or a restriction fragment; (4) recombinant DNAs; and (5) synthetic DNAs. An isolated nucleic acid may also be comprised of one or more segments of cDNA, genomic DNA or synthetic DNA.

Stringent conditions are sequence dependent and will be different in different circumstances. Generally, stringent conditions are selected to be about 5° C. lower than the thermal melting point (Tm) for the specific sequence at a defined ionic strength and pH. The Tm is the temperature (under defined ionic strength and pH) at which 50% of the target sequence hybridizes to a perfectly matched probe. Appropriate stringent conditions are known to those skilled in the art or can be found in *Current Protocols in Molecular Biology*, John Wiley & Sons, N.Y. 6.3.1-6.3.6 (1989). For the purposes of this disclosure, stringent conditions include at least one wash (usually 2) in 0.2×SSC at a temperature of at least about 50° C., usually about 55° C., for 20 minutes, or equivalent conditions.

The hybridizing portion of two different but at least partly complementary nucleic acids is at least about 20 nucleotides in length, or about 50 nucleotides in length, or least about 75 nucleotides in length, or even at least about 100 nucleotides or longer. As used herein, the hybridizing portion a given nucleic acid sequence or segment exhibits at least from about 70% to about 100% identity to a portion of a sequence as set forth in SEQ ID NO:1 to SEQ ID NO:5313, or any sequence as set forth in SEQ ID NO:10617 to SEQ ID NO:14985.

As used herein, an "open reading frame" (ORF) is a segment of a nucleotide sequence that encodes a polypeptide. Open reading frames in genomic sequences can be screened for the presence of protein homologues utilizing one or a number of different search algorithms that have been developed, one example of which are the suite of programs referred to as BLAST programs. Nucleic acids derived from *Xenorhabdus* species of bacteria commonly symbiotically associated with insect pathogenic *Steinernema* nematodes are surprisingly useful in providing compositions comprising insect inhibitory proteins, microbial inhibitory proteins including bactericidal, bacteriostatic, fungicidal, and fungistatic proteins, protein homologs of chitinases, histones and restriction enzymes, proteases, proteins capable of conferring resistance to heavy metals or other toxic compositions, proteins and compositions capable of conferring pharmaceutical advantages such as antineoplastic, acaricidal, anti-inflammatory and anti-ulcerogenic properties, polyketide synthases, transposons and mobile genetic elements and their corresponding transposases, excisases, integrases, and invertases, phage and phage particle proteins, other useful proteins homologous to proteins derived from *Xenorhabdus, Photorhabdus, Serratia, Yersinia, Salmonella, E. coli,* and *Erwinia* sp. among others. In addition, antibodies directed to the above-mentioned proteins and fragments thereof have been discovered to be of particular utility in the present invention.

The present invention provides an isolated protein having an amino acid sequence that is substantially identical to a member selected from group consisting of SEQ ID NO:5314 through SEQ ID NO:10626. By "substantially identical" or "substantial identity" as used in reference to two amino acid sequences, it is meant that one amino acid sequence is identical to the other amino acid sequence or exhibits at least about 50% sequence identity, at least about 70% sequence identity, at least about 80%, at least about 90%, or at least about 95% identity or greater, or any range in between, when compared to another amino acid sequence as a reference sequence using the programs described herein, preferably BLASTP using standard parameters, as described below. "Sequence identity" is determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

Polypeptides that are substantially similar share sequences in which residue positions are not identical and may differ by conservative amino acid changes. Conservative amino acid substitutions refer to the interchangeability of residues having similar side chains. "Conservative amino acid substitutions" refer to substitutions of one or more amino acids in a native amino acid sequence with another amino acid(s) having similar side chains, resulting in a silent change. Conserved substitutes for an amino acid within a native amino acid sequence can be selected from other members of the group to which the naturally occurring amino acid belongs.

Optimal alignment of sequences for comparison can use any means to analyze sequence identity (homology) known in the art, e.g., by the BLAST algorithm (Altschul et al, J. Mol. Biol. 215: 403-410, 1990) that is suitable for determining sequence similarity; by the progressive alignment method of termed "PILEUP" (Morrison, Mol. Biol. Evol. 14:428-441, 1997); and by the local homology algorithm of Smith & Waterman (Adv. Appl. Math. 2: 482, 1981). Software for performing BLAST analyses is publicly available through the National Center for Biotechnology Information (NCBI). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

One skilled in the art will recognize that a value of sequence identity can be appropriately adjusted to determine corresponding sequence identity of two nucleotide sequences encoding the proteins of the present invention by taking into account codon degeneracy, conservative amino acid substitutions, reading frame positioning and the like. Substantial identity of nucleotide sequences for these purposes normally means sequence identity between at least two different sequences exhibiting at least about 50%, at least about 60%, at least about 70%, at least about 80%, at least about 90%, or at least about 95% or greater or any range inbetween to a reference sequence or to each other.

The isolated nucleic acid molecule of the present invention can encode an insect inhibitory protein. In particular, the amino acid sequences as set forth at SEQ ID NO:7316, SEQ ID NO:9584, SEQ ID NO:9585, SEQ ID NO:9639 and SEQ ID NO:9679 each respectively encoded by the nucleotide sequences as set forth at SEQ ID NO:2003, SEQ ID NO:4271, SEQ ID NO:4272, SEQ ID NO:4326 and SEQ ID NO:4366 encode insecticidal proteins. The term "insecticidal" or "insect inhibitory protein" refers to any polypeptide or protein or portion thereof that exhibits insect inhibitory activity when provided in the diet of a target insect. The activity may be manifested by an observation that the presence of the insecticidal agent inhibits the growth or development of, or the contributes substantially to, or causes the death of a Coleopteran, a Dipteran, a Lepidopteran, a Hemipteran, a Hymenopteran, or a sucking and piercing insect, or any combination thereof, and includes any polypeptide or protein derived from the above mentioned sequences, whether the sequence has been mutated, truncated, contains an insertion or deletion, or otherwise, so long as the agent maintains at least the insect inhibitory activity associated with the native composition. Accordingly, the isolated nucleic acids encoding those polypeptide or protein with such modification are also within the scope of the present invention.

The insect inhibitory proteins of the present invention have been shown by BLAST analysis to exhibit homology to other previously identified *Xenorhabdus* or *Photorhabdus* insecticidal proteins. For instance, the polypeptide sequence as set forth in SEQ ID NO:7316 exhibits about 60% amino acid sequence homology to an insecticidal toxin complex protein TcaC from *Photorhabdus luminescens laumondii*. The polypeptide sequence as set forth in SEQ ID NO:9584 exhibits 81% amino acid sequence homology to an insecticidal toxin A2 from *Xenorhabdus nematophila*. The polypeptide sequence as set forth in SEQ ID NO:9585 exhibits 57% amino acid sequence homology to an insecticidal toxin complex protein TcaC from *Photorhabdus luminescens*. The polypeptide sequence as set forth in SEQ ID NO:9639 exhibits 69% amino acid sequence homology to an insecticidal toxin complex protein TcdB1 from *Photorhabdus luminescens laumondii*. The polypeptide sequence as set forth in SEQ ID NO:9679 exhibits 69% amino acid sequence homology to an insecticidal toxin complex protein TccC from *Photorhabdus luminescens*.

There is growing interest within the medical sciences in the potential utility of purified mammalian antibodies in the diagnosis and treatment of disease. For example, tagged antibodies directed against tumor cell surface antigens provide a highly sensitive and specific means for detecting and classifying various cancers. One therapeutic application using antibodies involves the administration of purified tumor-specific antibodies that are chemically coupled to cytotoxic agents. A class of cytotoxins that holds particular promise in the treatment of cancers consists of protein toxins from plants. However, progress in the treatment of cancers using chemically coupled antibodies and cytotoxins has been impeded by the lack of a cost effective means for producing these molecules in a pharmaceutically acceptable grade and in commercially acceptable quantities. Cytotoxin homologs may be overexpressed in plants and large quantities of the cytotoxin proteins may be produced, isolated and purified from the plants. These purified plant toxins may be used as a therapeutic agents. Cytotoxin protein homologues have been identified from sequences present in the genome of the Xenorhabdus strain Xs85831. Cytotoxin protein homologues are represented by the amino acid sequences as set forth in the following sequences: SEQ ID NO:5524, SEQ ID NO:5845, SEQ ID NO:5846, SEQ ID NO:5901, SEQ ID NO:5932, SEQ ID NO:5975, SEQ ID NO:6700, SEQ ID NO:7023, SEQ ID NO:7373, SEQ ID NO:7374, SEQ ID NO:7375, SEQ ID NO:7377, SEQ ID NO:7563, SEQ ID NO:7877, SEQ ID NO:8566, SEQ ID NO:8624, SEQ ID NO:8632, SEQ ID NO:8721, SEQ ID NO:8735, SEQ ID NO:9429, SEQ ID NO:9628, SEQ ID NO:9704, SEQ ID NO:9738, SEQ ID NO:9774, SEQ ID NO:9777, SEQ ID NO:9779, SEQ ID NO:9833, SEQ ID NO:10005, SEQ ID NO:10322, SEQ ID NO:10368, SEQ ID NO:10598 and SEQ ID NO:10605.

Polyketides are small bioactive molecules that are a class of small compounds linked by their biosynthetic pathways. The pathways and their products are particularly abundant in soil microorganisms. A large number of major pharmaceutical and agricultural products have been derived from these complex natural products including insecticides, fungicides, antibacterials, anti-inflammatory, cancer-fighting agents, and cholesterol-lowering agents. Examples of polyketides include Rifamycins (Rifampin), Adriamycin (Doxorubicin), Erythromycin, Mevacor (Lovastatin), Ascomycin (Immunomycin), and Spinosad. Polyketides are produced by large proteins referred to as polyketide synthases (or synthetases). There are an extraordinary number of polyketides synthase genes in the genome of Xenorhabdus bovienii strain Xs85831. In addition to polyketide synthases Xenorhabdus also contains an extraordinary number of related proteins referred to as non-ribosomal peptide synthases (NRP synthase). These proteins also generate small molecules with a variety of biochemical functions. It is possible that any of these genes can be placed into the genome of a plant to produce a substance (polyketide or non-ribosomal peptide) that can protect a plant against damage from insects, fungi, or bacteria. In addition, these genes can be placed in plants to generate polyketides or non-ribosomal peptides for other uses including pharmaceuticals. Polyketide synthase protein homologues have been identified in the genome of the present invention and are set forth at SEQ ID NO:6034, SEQ ID NO:6035, SEQ ID NO:6037, SEQ ID NO:6038, SEQ ID NO:6040, SEQ ID NO:6041, SEQ ID NO:6042, SEQ ID NO:6817, SEQ ID NO:7170, SEQ ID NO:7360, SEQ ID NO:7361, SEQ ID NO:7362, SEQ ID NO:7363, SEQ ID NO:7550, SEQ ID NO:8093, SEQ ID NO:8094, SEQ ID NO:8095, SEQ ID NO:8186, SEQ ID NO:8686, SEQ ID NO:8687, SEQ ID NO:9049, SEQ ID NO:9100, SEQ ID NO:9101, SEQ ID NO:9104, SEQ ID NO:9108, SEQ ID NO:9322, SEQ ID NO:9324, SEQ ID NO:10039, SEQ ID NO:10228, SEQ ID NO:10229, SEQ ID NO:10257 and SEQ ID NO:10258.

Proteases play very important roles in an organism's metabolism and proteins synthesis and several types of proteases have been reported. A processing protease is a protease that cleaves a propeptide to generate a mature biochemically active polypeptide (Enderlin and Ogrydziak, Yeast 10:67-79, 1994). Serine protease is required for intramitochondrial proteolysis and maintenance of respiratory function. Ubiquitin-specific protease (ubiquitin C-terminal hydrolase) of the 26S proteasome complex is involved in vacuole biogenesis and osmoregulation. Inner membrane protease of mitochondria acts in complex with IMP1P but has different substrate specificity for removal of signal peptidase serine protease of the subtilisin family with broad proteolytic specificity (U.S. Pat. No. 6,723,837). A number of protease homologues were identified as being encoded from various genes in the genome of Xenorhabdus bovienii strain Xs85831 as set forth in the sequence listing at SEQ ID NO:5589, SEQ ID NO:5625, SEQ ID NO:5958, SEQ ID NO:5959, SEQ ID NO:6156, SEQ ID NO:6298, SEQ ID NO:6300, SEQ ID NO:6404, SEQ ID NO:6530, SEQ ID NO:6602, SEQ ID NO:6839, SEQ ID NO:7599, SEQ ID NO:7682, SEQ ID NO:7706, SEQ ID NO:7735, SEQ ID NO:7737, SEQ ID NO:7941, SEQ ID NO:7999, SEQ ID NO:8072, SEQ ID NO:8137, SEQ ID NO:8267, SEQ ID NO:8568, SEQ ID NO:9284, SEQ ID NO:9336, SEQ ID NO:9368, SEQ ID NO:9729, SEQ ID NO:9921, SEQ ID NO:9984, SEQ ID NO:10021, SEQ ID NO:10022, SEQ ID NO:10143, SEQ ID NO:10201, SEQ ID NO:10263, SEQ ID NO:10327, SEQ ID NO:10371, SEQ ID NO:10372, SEQ ID NO:10411, SEQ ID NO:10412, SEQ ID NO:10413, SEQ ID NO:10430, SEQ ID NO:10580 and SEQ ID NO:10582.

A chitinase is one of several classes of antifungal proteins that include chitinases, defensins, cysteine-rich chitin-binding proteins, β-1,3-glucanases, permatins (including zeamatins), thionins, ribosome-inactivating proteins, and non-specific lipid transfer proteins (U.S. Pat. No. 6,573,361). A number of chitinase or related homologues were identified as being encoded from various genes in the genome of Xenorhabdus bovienii strain Xs85831 as set forth in the sequence listing at SEQ ID NO:6895, SEQ ID NO:8218, SEQ ID NO:8222, SEQ ID NO:10427 and SEQ ID NO:10583.

"Restriction enzyme" refers to an enzyme that recognizes a specific palindromic or other sequence of nucleotides in double stranded DNA and cleaves both strands. Nucleotide sequences encoding unique restriction enzymes and their corresponding modification methylase homologues are useful in the biological arts. A number of restriction enzymes and modification methylases and proteins homologous to such enzymes were identified as being encoded from various genes in the genome of Xenorhabdus bovienii strain Xs85831 as set forth in the sequence listing at SEQ ID NO:6835, SEQ ID NO:7488, SEQ ID NO:8128, SEQ ID NO:8129, SEQ ID NO:8132, SEQ ID NO:8901, SEQ ID NO:8902, SEQ ID NO:8903 and SEQ ID NO:9854.

Histones are abundant and required for DNA organization in all eukaryotes. Genes with homology to histones and proteins that affect histones, such histone deacetylases may affect histones in insects, disrupting normal cellular processes. Histones have not previously been found in bacteria. Surprisingly, various genes capable of encoding histone and histone deacetylase homologous proteins were found to be present in the genome of Xenorhabdus bovienii strain Xs85831 as set forth in the sequence listing at SEQ ID NO:5672, SEQ ID NO:5923, SEQ ID NO:6188, SEQ ID NO:7790, SEQ ID NO:7816, SEQ ID NO:7835, SEQ ID NO:8060, SEQ ID NO:9246, SEQ ID NO:9672, SEQ ID NO:9907, SEQ ID NO:9916, SEQ ID NO:10115, SEQ ID NO:10199, SEQ ID NO:10517 and SEQ ID NO:10540.

Ferritin homologuous proteins are encoded by various open reading frames within the genome of Xenorhabdus bovienii strain Xs85831 as set forth in the sequence listing at SEQ ID NO:5769, SEQ ID NO:5770, SEQ ID NO:6289 and SEQ ID NO:7552. These proteins may be used for overexpression in plants, resulting in an increase in resistance to abiotic and biotic oxidative stresses. Overexpression of ferritin promotes cellular productivity during limited water conditions to prevent formation of oxygen radicals (US Pat. Appl. Pub. No. 20030233670).

Biopolymer transport protein homologues were identified as being expressible from the genome of *Xenorhabdus bovienii* strain Xs85831 as set forth at SEQ ID NO:5799, SEQ ID NO:5801, SEQ ID NO:5802, SEQ ID NO:10481 and SEQ ID NO:10482.

Protein homologues capable of conferring resistance to heavy metals were identified from translation of open reading frames in *Xenorhabdus bovienii* strain Xs85831 as set forth in SEQ ID NO:6291, SEQ ID NO:6521, SEQ ID NO:7064, SEQ ID NO:7069, SEQ ID NO:7726, SEQ ID NO:7727, SEQ ID NO:7729, SEQ ID NO:7962, SEQ ID NO:8108, SEQ ID NO:8284, SEQ ID NO:10189, SEQ ID NO:10190, SEQ ID NO:10326 and SEQ ID NO:10406. Such proteins may be introduced into crop plants to provide for resistance to heavy metals (U.S. Pat. No. 6,426,447).

Helicases are proteins involved in unwinding DNA. HrpA hlicase is associated with the plant pathogenic bacteria *Pseudomonas syringae*. Hrp-like helicase homologues were identified from translation of *Xenorhabdus bovienii* strain Xs85831 coding sequences. SEQ ID NO:8465 and SEQ ID NO:10227 may represent HrpA helicases of *Xenorhabdus* that could be useful in plant DNA metabolism for improving plant transformation or as a herbicide to affect DNA metabolism or gene regulation in plants.

Coding sequences encoding an *Anopheles* mosquito species homologous protein were identified from the genome of *Xenorhabdus bovienii* strain Xs85831 as set forth in SEQ ID NO:9502 and SEQ ID NO:9512. Bacteria do not normally have genes encoding proteins that exhibit high homology to insect proteins, so it is possible that these proteins may be associated with pathogenesis of mosquitos. These and other proteins such as histones and histone deacetylases may be acting during pathogenesis and/or infection of an insect by the *Steinernema/Xenorhabdus* complex to destroy or redirect insect regulatory pathways.

As used herein, the term "promoter" or "promoter sequence" refers to a nucleotide sequence that, when located in cis to a structural nucleotide sequence encoding a polypeptide, protein, RNA or otherwise, functions in a way that directs expression of one or more mRNA or other RNA molecules that encodes the polypeptide or protein or that folds into a structure that is used for structural or functional purposes such as a tRNA or a rRNA. Such promoter regions are typically found upstream of the trinucleotide, ATG, at the start site of a polypeptide-coding region. Promoter molecules can also include DNA sequences from which transcription of tRNA or rRNA sequences are initiated. Promoter sequences or regulatory elements identified from the genome of *Xenorhabdus bovienii* strain Xs85831 are set forth at SEQ ID NO:10627 through SEQ ID NO:13014.

The term "terminator sequence" refers to a nucleotide sequence that is required for the termination reaction of the transcription process. Termination involves recognition of the point at which no further bases should be added to a growing RNA chain. To terminate transcription, the formation of phosphodiester bonds must cease and the transcription complex must come apart. When the last base is added to the RNA chain, the RNA-DNA hybrid is disrupted, the DNA reforms into a duplex state, and the RNA polymerase enzyme and RNA molecule are both released from the DNA. Terminator sequences identified from the genome of *Xenorhabdus bovienii* strain Xs85831 are set forth at SEQ ID NO:13015 through SEQ ID NO:14450.

Sequences encoding ribosomal RNA (rRNA) and transfer RNA (tRNA) molecule homologous sequences were identified from an examination of *Xenorhabdus bovienii* strain Xs85831 genome sequences and are set forth at SEQ ID NO:14451 through SEQ ID NO:14541.

A "substantial portion" of a nucleotide sequence comprises enough of the sequence to afford specific identification and/or isolation of a nucleic acid fragment comprising the sequence. In general, gene specific oligonucleotide probes comprising 20-30 contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12-15 bases may be used as amplification primers in PCR in order to obtain a particular nucleic acid fragment comprising the primers. The skilled artisan, having the benefit of the sequences as reported herein, may now use all or a substantial portion of the disclosed sequences for purposes known to him or her in this art. Accordingly, the present invention comprises the complete sequences as reported in the accompanying Sequence Listing, as well as substantial portions of those sequences as defined above.

The nucleic acids of the present invention may be used to isolate nucleic acids encoding homologous proteins from the same or other species, such as *Photorhabdus, Serratia, Yersinia, Salmonella, E. coli, Bacillus*, and *Erwinia* species. Examples of sequence-dependent protocols include, but are not limited to, methods of nucleic acid hybridization, and methods of DNA and RNA amplification as exemplified by various uses of nucleic acid amplification technologies (e.g., polymerase chain reaction, ligase chain reaction).

Genes encoding homologous proteins, either as cDNAs or genomic DNAs, could be isolated directly by using all or a portion of the nucleic acids of the present invention as DNA hybridization probes to screen cDNA or genomic libraries from any desired organism employing methodology well known to those skilled in the art. Methods for forming such libraries are well known in the art (Sambrook et al., ibid). Specific oligonucleotide probes based upon the nucleic acids of the present invention can be designed and synthesized by methods known in the art. Moreover, the entire sequences of the nucleic acids can be used directly to synthesize DNA probes by methods known to the skilled artisan such as random primer DNA labeling, nick translation, or end-labeling techniques, or RNA probes using available in vitro transcription systems. In addition, specific primers can be designed and used to amplify a part or all of the sequences. The resulting amplification products can be labeled directly during amplification reactions or labeled after amplification reactions, and used as probes to isolate full-length cDNA or genomic DNAs under conditions of appropriate stringency.

In addition, two short segments of the nucleic acids of the present invention may be used in polymerase chain reaction protocols, for example, the RACE protocol (Frohman et al., Proc. Natl. Acad. Sci. USA 85:8998, 1988), to amplify longer nucleic acids encoding homologous genes from DNA or RNA from other sources.

Nucleic acids of interest may also be synthesized, either completely or in part, especially where it is desirable to provide a sequence that is functional in a plant cell, by well-known techniques as described in the technical literature. See, e.g., Carruthers et al. (Cold Spring Harbor Symp. Quant. Biol. 47:411-418, 1982) and Adams et al. (J. Am. Chem. Soc. 105:661, 1983).

Availability of the nucleotide sequences encoding *Xenorhabdus* proteins facilitates immunological screening of DNA expression libraries. Synthetic polypeptides representing portions of the amino acid sequences of *Xenorhabdus* proteins may be synthesized. These polypeptides can be used to immunize animals to produce polyclonal or monoclonal antibodies with specificity for polypeptides or proteins comprising the amino acid sequences. These antibodies can be then be used to screen expression libraries to isolate genes of interest.

The present invention provides substantially purified proteins or polypeptide molecules comprising an amino acid sequence that (1) is encoded by a nucleotide sequence that is at least about 50% identical to a coding sequence as set forth in any of SEQ ID NO:1 through SEQ ID NO:5313; or (2) is substantially identical to an amino acid sequence selected from the group consisting of SEQ ID NO:5314 to SEQ ID NO:10626.

The term "substantially purified protein or polypeptide molecule" refers to a protein or polypeptide molecule separated from substantially all other molecules normally associated with it in its native state. More preferably a substantially purified protein or polypeptide molecule is the predominant species present in a preparation. A substantially purified molecule may be greater than about 60%, or at least about 75%, or at least about 80%, at least about 90%, or at least about 95% free from the other molecules (exclusive of solvent) present as found in its natural environment.

Proteins or polypeptides may undergo modifications, including post-translational modifications, such as, but not limited to, disulfide bond formation, glycosylation, phosphorylation, or oligomerization. Thus, as used herein, the term "protein molecule" or "polypeptide molecule" includes any protein molecule that is modified by any biological or non-biological process. The terms "amino acid" and "amino acids" refer to all naturally occurring amino acids. This definition is meant to include norleucine, ornithine, homocysteine, and homoserine.

The polypeptides or proteins of the present invention may be produced via chemical synthesis, or more preferably, by expression in a suitable bacterial or eukaryotic host. Suitable methods for expression of the polypeptides or proteins are described by Sambrook et al. (ibid). The polypeptides or protein molecules of the present invention may also include fusion protein or polypeptide molecules. A protein or polypeptide molecule that comprises one or more additional polypeptide regions not derived from that protein molecule is a "fusion" protein or polypeptide molecule. Such molecules may be derivatized to contain carbohydrate or other moieties (such as keyhole limpet hemocyanin, etc.). Fusion protein or polypeptide molecules of the present invention are preferably produced via recombinant means.

Antibodies may be used to quantitatively or qualitatively detect the protein or polypeptide molecules of the present invention. As used herein, an antibody or polypeptide is said to "specifically bind" to a protein or polypeptide molecule of the present invention if such binding is not competitively inhibited by the presence of non-related molecules.

Nucleic acid molecules that encode all or part of the protein or polypeptide of the present invention can be expressed, via recombinant means, to yield protein or polypeptides that can in turn be used to elicit antibodies that are capable of binding the expressed protein or polypeptide. Such antibodies may be used in immunoassays for that protein or polypeptide. Such protein or polypeptide-encoding molecules, or their fragments may be "fusion" molecules (i.e., a part of a larger nucleic acid molecule) such that, upon expression, a fusion protein is produced. It may be desirable to derivatize the obtained antibodies, for example, with a ligand group (such as biotin) or a detectable marker group (such as a fluorescent group, a radioisotope or an enzyme). Such antibodies may be used in immunoassays for that protein or may be used to screen DNA expression libraries to isolate clones containing full-length insert of genes.

Antibodies elicited in response to challenge with amino acid sequences selected from the group consisting of SEQ ID NO:7316, SEQ ID NO:9584, SEQ ID NO:9585, SEQ ID NO:9639 and SEQ ID NO:9679 can be used to specifically bind to one or more of these insect inhibitory polypeptides or proteins and to detect homologous sequences produced by other organisms, including but not limited to other *Xenorhabdus* species, and to detect the presence of such insect inhibitory polypeptides or proteins in a sample.

The present invention also provides a method for detecting an insect inhibitory polypeptide or protein in a biological sample, the method comprising: (1) obtaining a biological sample; (2) contacting the sample with an antibody that specifically binds to the polypeptide or protein comprising any or all or any combination of SEQ ID NO:7316, SEQ ID NO:9584, SEQ ID NO:9585, SEQ ID NO:9639 and SEQ ID NO:9679, under conditions effective to allow the formation of immune complexes; and (3) detecting the complexes so formed.

A recombinant vector or construct for use in transformation of a plant cell is provided comprising a structural nucleotide sequence encoding a *Xenorhabdus* protein or polypeptide selected from the group consisting of SEQ ID NO:5313 through SEQ ID NO:10626. In a preferred embodiment, a plant recombinant vector or construct of the present invention comprises a structural nucleotide sequence encoding an insect inhibitory protein or polypeptide of the present invention comprising an amino acid sequence that is selected from the group consisting of SEQ ID NO:7316, SEQ ID NO:9584, SEQ ID NO:9585, SEQ ID NO:9639 and SEQ ID NO:9679. The present invention also relates to a transformed plant cell or plant comprising in its genome an exogenous nucleic acid encoding one or more *Xenorhabdus* proteins or polypeptides of the present invention. The present invention also relates to methods for creating a transgenic plant in which one or more *Xenorhabdus* proteins or polypeptides of the present invention are overexpressed.

As used herein, "structural nucleotide sequence" refers to a nucleotide sequence that is expressed to produce a polypeptide. The term "genome" as it applies to plant cells encompasses not only chromosomal DNA found within the nucleus, but organelle DNA found within subcellular components of the cell. DNA of the present invention introduced into plant cells can therefore be either chromosomally integrated or organelle-localized. The term "genome" as it applies to bacteria encompasses both the chromosome and plasmids within a bacterial host cell. DNA of the present invention introduced into bacterial host cells can therefore be either chromosomally integrated or plasmid-localized.

Methods that are well known to those skilled in the art may be used to construct the plant recombinant construct or vector of the present invention. These methods include in vitro recombinant DNA techniques, synthetic techniques, and in vivo genetic recombination. Such techniques are described in part at least in Sambrook et al. (ibid); and Ausubel et al. (Current Protocols in Mol. Biol., John, Wiley & Sons, New York, N.Y., 1989).

A plant recombinant construct or vector of the present invention contains a structural nucleotide sequence encoding one or more *Xenorhabdus* proteins or polypeptides of the present invention as set forth in SEQ ID NO:5313 through SEQ ID NO:10626 and operably linked regulatory sequences or control elements.

The term "operably linked", as used in reference to a regulatory sequence and a structural nucleotide sequence, means that the regulatory sequence causes regulated expression of the operably linked structural nucleotide sequence. "Regulatory sequences" or "control elements" refer to nucleotide sequences located upstream (5' noncoding sequences), within, or downstream (3' non-translated sequences) of a structural nucleotide sequence, and which influence the transcription, RNA processing or stability, or translation of the associated structural nucleotide sequence. Regulatory sequences may include promoters, translation leader sequences, introns, and polyadenylation recognition sequences.

It is understood that different promoters may direct the expression of a gene in different tissues or cell types, or at different stages of development, or in response to different environmental conditions. For example, promoters that may be used in the present invention include, but are not limited to, constitutive promoters [e.g., the nopaline synthase (NOS) promoters (Ellis et al., EMBO Journal 6:11-16, 1987); the cauliflower mosaic virus (CaMV) 35S (Fraley et al., U.S. Pat. No. 5,858,742); and actin promoters, such as the *Arabidopsis* actin gene promoter (see, e.g., Huang, Plant Mol. Biol. 33:125-139, 1997)], inducible promoter [e.g., the drought-inducible promoter of maize (Busk, Plant J. 11:1285-1295, 1997; the cold, drought, and high salt inducible promoter from potato (Kirch, Plant Mol. Biol. 33:897-909, 1997; and salicylic acid inducible promoter (Uknes et al., Plant Cell 5:159-169, 1993)] and tissue-specific promoters [e.g., leaf-specific promoters [e.g., Matsuoka, Plant J. 6:311-319, 1994; Shiina, Plant Physiol. 115-477-483, 1997); root-specific promoters (e.g., Samac et al., *Plant Mol. Biol.* 25: 587-596, 1994; Yamamoto, Plant Cell 3:371-382, 1991), tuber-specific promoters (Hannapel, *Plant Physiol.* 101: 703-704, 1993; Bevan et al., *EMBO J.* 8: 1899-1906, 1986), seed-specific promoters (e.g., Sheridan, Genetics 142:1009-1020, 1996; Abler, Plant Mol. Biol. 22:10131-1038, 1993) and pollen-specific promoter (e.g., Guerrero, Mol. Gen. Genet. 224:161-168, 1990; Wakeley, Plant Mol. Biol. 37:187-192, 1992).

It is recognized that additional promoters that may be utilized are described, for example, in U.S. Pat. Nos. 5,378,619, 5,391,725, 5,428,147, 5,447,858, 5,608,144, 5,608,144, 5,614,399, 5,633,441, 5,633,435, and 4,633,436. In addition, a tissue specific enhancer may be used (Fromm et al., *The Plant Cell* 1:977-984, 1989). It is further recognized that since in most cases the exact boundaries of regulatory sequences have not been completely defined, DNA fragments of different lengths may have identical promoter activity.

"Translation leader sequence" refers to a DNA sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences include maize and petunia heat shock protein leaders (U.S. Pat. No. 5,362,865), plant virus coat protein leaders, and plant rubisco leaders, among others (Turner and Foster, Molecular Biotechnology 3:225, 1995).

The 3' non-translated sequence or 3' transcription termination region means a DNA molecule linked to and located downstream of a structural polynucleotide molecule and includes polynucleotides that provide polyadenylation signal and other regulatory signals capable of affecting transcription, mRNA processing or gene expression. The polyadenylation signal functions in plants to cause the addition of polyadenylate nucleotides to the 3' end of the mRNA precursor. The polyadenylation sequence can be derived from the natural gene, from a variety of plant genes, or from T-DNA genes. An example of a 3' transcription termination region is the nopaline synthase 3' region (nos 3'; Fraley et al., Proc. Natl. Acad. Sci. USA, 80: 4803-4807, 1983). The use of different 3' nontranslated regions is exemplified by Ingelbrecht et al. (Plant Cell 1:671-680, 1989).

A recombinant vector or construct of the present invention will typically comprise a selectable marker that confers a selectable phenotype on plant cells. Selectable markers may also be used to select for plants or plant cells that contain the exogenous nucleic acids encoding polypeptides or proteins of the present invention. The marker may encode biocide resistance, antibiotic resistance (e.g., kanamycin, G418 bleomycin, hygromycin, etc.), or herbicide resistance (e.g., glyphosate, etc.). Examples of selectable markers include, but are not limited to, a neo gene (Potrykus et al., *Mol. Gen. Genet.* 199:183-188, 1985) which codes for kanamycin resistance and can be selected for using kanamycin, G418, etc.; a mutant EPSP synthase gene (Hinchee et al., *Bio/Technology* 6:915-922, 1988) which encodes glyphosate resistance; and a nitrilase gene which confers resistance to bromoxynil (Stalker et al., *J. Biol. Chem.* 263:6310-6314, 1988).

A recombinant vector or construct of the present invention may also include a screenable marker. Screenable markers may be used to monitor expression. Exemplary screenable markers include a β-glucuronidase or uidA gene (GUS) which encodes an enzyme for which various chromogenic substrates are known (Jefferson, *Plant Mol. Biol, Rep.* 5:387-405, 1987; Jefferson et al., *EMBO J.* 6:3901-3907, 1987); an R-locus gene (Dellaporta et al., Stadler Symposium 11:263-282, 1988); a β-lactamase gene (Sutcliffe et al., *Proc. Natl. Acad. Sci. (U.S.A.)* 75:3737-3741, 1978); and a luciferase gene (Ow et al., *Science* 234:856-859, 1986). Included within the terms "selectable or screenable marker genes" are also genes that encode a secretable marker whose secretion can be detected as a means of identifying or selecting for transformed cells. Examples include markers that encode a secretable antigen that can be identified by antibody interaction, or even secretable enzymes that can be detected catalytically. Secretable proteins fall into a number of classes, including small, diffusible proteins detectable, e.g., by ELISA, small active enzymes detectable in extracellular solution (e.g., α-amylase, β-lactamase, phosphinothricin transferase), or proteins which are inserted or trapped in the cell wall (such as proteins which include a leader sequence such as that found in the expression unit of extension or tobacco PR-S). Other possible selectable and/or screenable marker genes will be apparent to those of skill in the art.

In preparing the DNA constructs of the present invention, the various components of the construct or fragments thereof will normally be inserted into a convenient cloning vector, e.g., a plasmid that is capable of replication in a bacterial host, e.g., *E. coli*. Numerous vectors exist that have been described in the literature, many of which are commercially available. After each cloning, the cloning vector with the desired insert may be isolated and subjected to further manipulation, such as restriction digestion, insertion of new fragments or nucleotides, ligation, deletion, mutation, resection, etc. so as to tailor the components of the desired sequence. Once the construct has been completed, it may then be transferred to an appropriate vector for further manipulation in accordance with the manner of transformation of the host cell.

The present invention also provide a transgenic plant comprising in its genome an isolated nucleic acid which comprises: (1) a 5' non-coding sequence which functions in the cell to cause the production of a mRNA molecule; which is linked to (2) a structural nucleotide sequence, wherein the structural nucleotide sequence encodes a *Xenorhabdus* protein or polypeptide of the present invention that is substantially identical to a member selected from the group consisting of SEQ ID NO:5314 to SEQ ID NO:10626; which is linked to (3) a 3' non-translated sequence that functions in said cell to cause termination of transcription.

The term "transgenic plant" refers to a plant that contains an exogenous nucleic acid, which can be derived from the same plant species or from a different plant species. Transgenic plants of the present invention preferably have incorporated into their genome or transformed into their chloroplast or plastid genomes a selected polynucleotide (or "transgene"), that comprises at least a structural nucleotide sequence that encodes a polypeptide the amino acid sequence of which is selected from the group consisting of SEQ ID NO:5314 to SEQ ID NO:10626 or, in particular, an insect inhibitory polypeptide the amino acid sequence of which is selected from the group consisting of SEQ ID NO:7316, SEQ ID NO:9584, SEQ ID NO:9585, SEQ ID NO:9639 and SEQ ID NO:9679, which are also referred to herein as XIP or Xip proteins (*Xenorhabdus* Insecticidal Proteins), the genes encoding such proteins as xip genes. Transgenic plants are also meant to comprise progeny (decendant, offspring, etc.) of any generation of such a transgenic plant. A seed of any generation of such transgenic insect-resistant plants is also an important aspect of the invention so long as the cells of the seed contain the DNA sequence encoding the *Xenorhabdus* polypeptide.

The DNA constructs of the present invention may be introduced into the genome of a desired plant host by a variety of conventional transformation techniques, which are well known to those skilled in the art. Preferred methods of transformation of plant cells or tissues are the *Agrobacterium* mediated transformation method and the biolistics or particle-gun mediated transformation method. Suitable plant transformation vectors for the purpose of *Agrobacterium* mediated transformation include those derived from a Ti plasmid of *Agrobacterium tumefaciens*, as well as those disclosed, e.g., by Herrera-Estrella et al. (Nature 303:209, 1983); Bevan (Nucleic Acids Res. 12: 8711-8721, 1984); Klee et al. (Bio-Technology 3(7): 637-642, 1985); and EPO publication 120,516. In addition to plant transformation vectors derived from the Ti or root-inducing (Ri) plasmids of *Agrobacterium*, alternative methods can be used to insert the DNA constructs of this invention into plant cells. Such methods may involve, but are not limited to, for example, the use of liposomes, electroporation, chemicals that increase free DNA uptake, free DNA delivery via microprojectile bombardment, and transformation using viruses or pollen.

A plasmid expression vector suitable for the introduction of a nucleic acid encoding a polypeptide or protein of the present invention in monocots using electroporation or particle-gun mediated transformation is composed of the following: a promoter that is constitutive or tissue-specific; an intron that provides a splice site to facilitate expression of the gene, such as the Hsp70 intron (PCT Publication WO93/19189); and a 3' polyadenylation sequence such as the nopaline synthase 3' sequence (NOS 3'; Fraley et al., Proc. Natl. Acad. Sci. USA 80: 4803-4807, 1983). This expression cassette may be assembled on high copy replicons suitable for the production of large quantities of DNA.

When adequate numbers of cells (or protoplasts) containing the exogenous nucleic acid encoding a polypeptide or protein of the present invention are obtained, the cells (or protoplasts) are regenerated into whole plants. Choice of methodology for the regeneration step is not critical, with suitable protocols being available for hosts from Leguminosae (alfalfa, soybean, clover, etc.), Umbelliferae (carrot, celery, parsnip), Cruciferae (cabbage, radish, canola/rapeseed, etc.), Cucurbitaceae (melons and cucumber), Gramineae (wheat, barley, rice, maize, etc.), Solanaceae (potato, tobacco, tomato, peppers), various floral crops, such as sunflower, and nut-bearing trees, such as almonds, cashews, walnuts, and pecans. See, for example, Ammirato et al. (Handbook of Plant Cell Culture—Crop Species. Macmillan Publ. Co., 1984); Shimamoto et al (Nature 338:274-276, 1989); Vasil et al. (Bio/Technology 8:429-434, 1990; Bio/Technology 10:667-674, 1992); Hayashimoto (Plant Physiol. 93:857-863, 1990); and Datta et al. (Bio-technology 8:736-740, 1990). Regeneration can also be obtained from plant callus, explants, organs, or parts thereof. Such regeneration techniques are described generally in Klee et al. (Ann. Rev. Plant Phys. 38:467-486, 1987).

A transgenic plant formed using *Agrobacterium* transformation methods typically contains a single exogenous gene on one chromosome. Such transgenic plants can be referred to as being heterozygous for the added exogenous gene. More preferred is a transgenic plant that is homozygous for the added exogenous gene; i.e., a transgenic plant that contains two added exogenous genes, one gene at the same locus on each chromosome of a chromosome pair. A homozygous transgenic plant can be obtained by sexually mating (selfing) an independent segregant transgenic plant that contains a single exogenous gene, germinating some of the seeds produced and analyzing the resulting plants produced for the exogenous gene of interest.

The development or regeneration of transgenic plants containing the exogenous nucleic acid that encodes a polypeptide or protein of interest is well known in the art. Preferably, the regenerated plants are self-pollinated to provide homozygous transgenic plants, as discussed above. Otherwise, pollen obtained from the regenerated plants is crossed to seed-grown plants of agronomically important lines. Conversely, pollen from plants of these important lines is used to pollinate regenerated plants. A transgenic plant of the present invention containing a desired polypeptide or protein of the present invention is cultivated using methods well known to one skilled in the art.

Transgenic plants, that can be generated by practice of the present invention, include but are not limited to *Acacia*, alfalfa, aneth, apple, apricot, artichoke, arugula, asparagus, avocado, banana, barley, beans, beet, blackberry, blueberry, broccoli, brussels sprouts, cabbage, canola, cantaloupe, carrot, cassaya, cauliflower, celery, cherry, cilantro, citrus, clementines, coffee, corn, cotton, cucumber, Douglas fir, eggplant, endive, escarole, eucalyptus, fennel, figs, gourd, grape, grapefruit, honey dew, jicama, kiwifruit, lettuce, leeks, lemon, lime, pine, mango, melon, mushroom, nut, oat, okra, onion, orange, an ornamental plant, papaya, parsley, pea, peach, peanut, pear, pepper, persimmon, pine, pineapple, plantain, plum, pomegranate, poplar, potato, pumpkin, quince, radiata pine, radicchio, radish, raspberry, rice, rye, sorghum, soybean, spinach, squash, strawberry, sugarbeet, sugarcane, sunflower, sweet potato, sweetgum, tangerine, tea, tobacco, tomato, turf, a vine, watermelon, wheat, yams, and zucchini.

The present invention also provides parts of the transgenic plants of present invention. Plant parts, without limitation, include seed, endosperm, ovule and pollen. In a particularly preferred embodiment of the present invention, the plant part is a seed.

The present invention also further provides method for generating a transgenic plant comprising the steps of: a) introducing into the genome of the plant an exogenous nucleic acid, wherein the exogenous nucleic acid comprises in the 5' to 3' direction i) a promoter that functions in the cells of said plant, said promoter operably linked to; ii) a structural nucleic acid sequence encoding a polypeptide or protein of the present invention that is selected from the group consisting of SEQ ID NO:5314 to SEQ ID NO:10626 or, in particular, an insect inhibitory polypeptide that is selected from the group consisting of SEQ ID NO:7316, SEQ ID NO:9584, SEQ ID NO:9585, SEQ ID NO:9639 and SEQ ID NO:9679, said structural nucleic acid sequence operably linked to; iii) a 3' non-translated nucleic acid sequence that functions in said cells of said plant to cause transcriptional termination; b) obtaining transformed plant cells containing the nucleic acid sequence of step (a); and c) regenerating from said transformed plant cells a transformed plant in which said polypeptide or protein is overexpressed.

Any of the isolated nucleic acid molecules of the present invention may be introduced into a plant cell in a permanent or transient manner in combination with other genetic elements such as vectors, promoters, enhancers etc. Further any of the nucleic acid molecules encoding a *Xenorhabdus* protein or polypeptide of the present invention may be introduced into a plant cell in a manner that allows for over expression of the protein or polypeptide encoded by the nucleic acid molecule.

The nucleotide sequences of the present invention may be introduced into a wide variety of prokaryotic and eukaryotic microorganism hosts to express the *Xenorhabdus* polypeptide or protein of the present invention, particularly the insect inhibitory polypeptides or proteins of the present invention comprising an amino acid sequence that is selected from the group consisting of SEQ ID NO:7316, SEQ ID NO:9584, SEQ ID NO:9585, SEQ ID NO:9639 and SEQ ID NO:9679. The term "microorganism" includes prokaryotic and eukaryotic microbial species such as bacteria and fungi. Illustrative prokaryotes, whether Gram-negative, Gram-positive, or otherwise, include Enterobacteriaceae, such as *Escherichia, Erwinia, Shigella, Salmonella,* and *Proteus*; Bacillaceae; Rhizobiceae, such as *Rhizobium*; Spirillaceae, such as *photobacterium, Zymomonas, Serratia, Aeromonas, Vibrio, Desulfovibrio, Spirillum*; Lactobacillaceae; Pseudomonadaceae, such as *Pseudomonas* and *Acetobacter*; Azotobacteraceae, Actinomycetales, and Nitrobacteraceae. Among eukaryotes are fungi, such as *Phycomycetes* and *Ascomycetes*, which includes yeast, such as *Saccharomyces* and *Schizosaccharomyces*; and *Basidiomycetes* yeast, such as *Rhodotorula, Aureobasidium, Sporobolomyces*, and the like.

For the purpose of plant protection against insects, a large number of microorganisms known to inhabit the phylloplane (the surface of the plant leaves) and/or the rhizosphere (the soil surrounding plant roots) of a wide variety of important crops may also be desirable host cells for manipulation, propagation, storage, delivery and/or mutagenesis of the disclosed recombinant constructs. These microorganisms include bacteria, algae, and fungi. Of particular interest are microorganisms, such as bacteria, e.g., genera *Bacillus* (including the species and subspecies); *Pseudomonas, Erwinia, Serratia, Klebsiella, Zanthomonas, Streptomyces, Rhizobium, Rhodopseudomonas, Methylophilius, Agrobacterium, Acetobacter, Lactobacillus, Arthrobacter, Azotobacter, Leuconostoc,* and *Alcaligenes*; fungi, particularly yeast, e.g., genera *Saccharomyces, Cryptococcus, Kluyveromyces, Sporobolomyces, Rhodotorula,* and *Aureobasidium*.

The present invention also relates to a bacterial or a fungal recombinant construct. The recombinant construct may comprise a structural nucleotide sequence encoding a *Xenorhabdus* protein or polypeptide comprising an amino acid sequence that is selected from the group consisting of SEQ ID NO:5314 to SEQ ID NO:10626. The present invention also relates to methods for obtaining a recombinant bacterial or fungal host cell, comprising introducing into a bacterial or fungal host cell an exogenous nucleic acid molecule that is selected from the group consisting of SEQ ID NO:1 to SEQ ID NO:5313.

The recombinant construct for producing a polypeptide in a bacterium also contains an inducible promoter that is recognized by the host bacterium and is operably linked to the nucleic acid encoding, for example, the nucleic acid molecule encoding the *Xenorhabdus* protein or polypeptide of interest. Inducible promoters suitable for use with bacterial hosts include the β-lactamase, *E. coli* λ phage $P_L$ and $P_R$, and *E. coli* galactose, arabinose, alkaline phosphatase, tryptophan (trp), and lactose operon promoter systems and variations thereof (Chang et al., *Nature* 275:615, 1978; Goeddel et al., *Nature* 281:544, 1979; Guzman et al., *J. Bacteriol.* 174:7716-7728, 1992; Goeddel, *Nucleic Acids Res.* 8:4057, 1980; EP 36,776). Hybrid promoters such as the tac promoter (deBoer et al., *Proc. Natl. Acad. Sci.* (*USA*) 80:21-25, 1983) and other known bacterial inducible promoters are suitable (Siebenlist et al., *Cell* 20:269, 1980) may also be used.

The bacterial recombinant construct or vector may be a linear or a closed circular plasmid. The vector system may be a single vector or plasmid or two or more vectors or plasmids that together contain the total DNA to be introduced into the genome of the bacterial host. In addition, the bacterial vector may be an expression vector. Nucleic acid molecules encoding *Xenorhabdus* proteins or polypeptide can, for example, be suitably inserted into a replicable vector for expression in a bacterium under the control of a suitable promoter for that bacterium. Many vectors are available for this purpose, and selection of the appropriate vector will depend mainly on the size of the nucleic acid to be inserted into the vector and the particular host cell to be transformed with the vector. Each vector contains various components depending on its function (amplification of DNA or expression of DNA) and the particular host cell with which it is compatible. The vector components for bacterial transformation generally include, but are not limited to, one or more of the following: a signal sequence, an origin of replication, one or more selectable marker genes, a promoter allowing the expression of an exogenous nucleotide sequence and a structural nucleotide sequence of the present invention.

In general, plasmid vectors containing replicon and control sequences that are derived from species compatible with the host cell are used in connection with bacterial hosts. The vector ordinarily carries a replication site, as well as marking sequences that are capable of providing phenotypic selection in transformed cells. For example, E. coli is typically transformed using pBR322, a plasmid derived from an *E. coli* species (see, e.g., Bolivar et al., *Gene* 2:95, 1977). The pBR322 plasmid contains genes for ampicillin and tetracycline resistance and thus provides easy means for identifying transformed cells. The pBR322 plasmid, or other microbial plasmid or phage, also generally contains, or is modified to contain, promoters that can be used by the microbial organism for expression of the selectable marker genes. In addition, nucleic acid molecules encoding *Xenorhabdus* proteins or polypeptides may be expressed not only directly, but also as a fusion with another polypeptide, preferably a signal sequence or other polypeptide having a specific cleavage site at the N-terminus of the mature polypeptide. The suitable vectors containing one or more of the above-listed components may be constructed employing standard recombinant DNA techniques. Isolated plasmids or DNA fragments are cleaved, tailored, and re-ligated in the form desired to generate the plasmids required. Examples of available bacterial expression vectors include, but are not limited to, the multifunctional *E. coli* cloning and expression vectors such as Bluescript™ (Stratagene, La Jolla, Calif.), in which, for example, a *Xenorhabdus* protein or polypeptide of the present invention, may be ligated into the vector in frame with sequences for the amino-terminal Met and the subsequent 7 residues of β-galactosidase so that a hybrid protein is produced; pIN vectors (Van Heeke and Schuster *J. Biol. Chem.* 264:5503-5509, 1989); and the like. pGEX vectors (Promega, Madison, Wis.) may also be used to express foreign polypeptides as fusion proteins with glutathione S-transferase (GST). Bacterial cells used to produce the polypeptide of interest for purposes of this invention are cultured in suitable media in which the promoters for the nucleic acid encoding the heterologous polypeptide can be artificially induced as described generally, e.g., in Sambrook et al., ibid). Examples of suitable media are given in U.S. Pat. Nos. 5,304,472 and 5,342,763.

A yeast recombinant construct can typically include one or more of the following: a promoter sequence, a fusion partner sequence, a leader sequence, a transcription termination sequence and a selectable marker. These elements can be combined into an expression cassette, which may be maintained in a replicon, such as an extrachromosomal element (e.g., plasmids) capable of stable maintenance in a host, such as yeast or bacteria. The replicon may have two replication systems, thus allowing it to be maintained, for example, in yeast for expression and in a procaryotic host for cloning and amplification. Examples of such yeast-bacteria shuttle vectors include YEp24 (Botstein et al., Gene, 8:17-24, 1979), pCl/1 (Brake et al., Proc. Natl. Acad. Sci. USA, 81:4642-4646, 1984), and YRp17 (Stinchcomb et al., J. Mol. Biol., 158:157, 1982).

The nucleotide sequence provided in the present invention can be "provided" in a variety of media to facilitate their use, and can be provided as a subset thereof in a form that allows a skilled artisan to examine the sequences.

In one application of this embodiment, a nucleotide sequence of the present invention can be recorded on computer readable media. As used herein, "computer readable media" refers to any medium that can be read and accessed directly by a computer. Such media include, but are not limited to: magnetic storage media, such as floppy discs, hard disc, storage medium, and magnetic tape: optical storage media such as CD-ROM; electrical storage media such as RAM and ROM; internet servers; and hybrids of these categories such as magnetic/optical storage media. The computer readable mediums can be used to create a manufacture comprising one or more computer readable media having recorded thereon one or more of the nucleotide sequences of the present invention.

By providing one or more of nucleotide sequences of the present invention, a skilled artisan can routinely access the sequence information for a variety of purposes. Computer software is publicly available which allows a skilled artisan to access sequence information provided in a computer readable medium. The examples which follow demonstrate how software which implements the BLAST (Altschul et al., *J. Mol. Biol.* 215:403-410, 1990) and BLAZE (Brutlag et al., *Comp. Chem.* 17:203-207, 1993) search algorithms on a Sybase system can be used to identify open reading frames (ORFs) within the genome that contain homology to ORFs or proteins from other organisms. Such ORFs are useful in producing commercially important proteins such as enzymes used in amino acid biosynthesis, metabolism, transcription, translation, RNA processing, nucleic acid and a protein degradation, protein modification, and DNA replication, restriction, modification, recombination, repair, designing sequences for incorporation into plasmids that are useful for modeling and testing prior to actually engaging in a costly procedure that can be very costly in terms of financial expenditures and human capital.

Nucleic acid molecules and fragments thereof of the present invention may be employed to obtain other nucleic acid molecules from the same or closely related species. Such nucleic acid molecules include the nucleic acid molecules that encode the complete coding sequence of a protein and promoters and flanking sequences of such molecules. In addition, such nucleic acid molecules include sequences that encode for other isozymes or gene family members. Such molecules can be readily obtained by using the above-described nucleic acid molecules or fragments thereof to screen genomic libraries obtained from *Xenorhabdus*.

The nucleic acid molecules of the present invention may be used for physical mapping in conjunction with linkage analysis, which can enable the isolation of genes. Physical mapping has been reported to identify the markers closest in terms of genetic recombination to a gene target for cloning. Once a DNA marker is linked to a gene of interest, the chromosome walking technique can be used to find the genes via overlapping clones. For chromosome walking, random molecular markers or established molecular linkage maps are used to conduct a search to localize the gene adjacent to one or more markers. A chromosome walk (Bukanov and Berg, *Mo. Microbiol.* 11:509-523, 1994; Birkenbihl and Vielmetter *Nucleic Acids Res.* 17:5057-5069, 1989; Wenzel and Herrmann, *Nucleic Acids Res.* 16:8323-8336, 1988) is then initiated from the closest linked marker. Starting from the selected clones, labeled probes specific for the ends of the insert DNA are synthesized and used as probes in hybridizations against a representative library. Clones hybridizing with one of the probes are picked and serve as templates for the synthesis of new probes; by subsequent analysis, contigs are produced. The degree of overlap of the hybridizing clones used to produce a contig can be determined by comparative restriction analysis. The most frequently used procedures are, fingerprinting (Coulson et al, *Proc. Natl. Acad. Sci.* (*U.S.A.*) 83:7821-7821, 1986; Knott et al., *Nucleic Acids Res.* 16:2601-2612, 1988; Eiglmeier et al., *Mol. Microbiol.* 7:197-206, 1993), restriction fragment mapping (Smith and Birnstiel, *Nucleic Acids Res.* 3:2387-2398, 1976), or the "landmarking" technique (Charlebois et al. *J. Mol. Biol.* 222:509-524, 1991).

Nucleic acid molecules of the present invention can be used to monitor expression. A microarray-based method for high-throughput monitoring of gene expression may be utilized to measure gene-specific hybridization targets. This 'chip'-based approach involves using microarrays of nucleic acid molecules as gene-specific hybridization targets to quantitatively measure expression of the corresponding genes (Schena et al., *Science* 270:467-470, 1995; Shalon, Ph.D. Thesis, Stanford University, 1996). Every nucleotide in a large sequence can be queried at the same time. Hybridization can be used to efficiently analyze nucleotide sequences. It is understood that one or more of the molecules of the present invention, preferably one or more of the nucleic acid molecules or protein molecules or fragments thereof of the present invention may be utilized in a microarray based method. In a preferred embodiment, the microarray of the present invention comprises at least 10 nucleic acid molecules, more preferably at least 100 nucleic acid molecules, and even more preferably at least 1000 nucleic acid molecules, that specifically hybridize under stringent conditions to at least 10, at least 100, at least 1000, nucleic acid molecules, respectively, encoding Xenorhabdus proteins or polypeptides or fragments thereof set forth in SEQ ID NO:1 through SEQ ID NO:5313 or fragment thereof or complement. In a further embodiment, the microarray of the present invention comprises at least 2,500 nucleic acid molecules that specifically hybridize under stringent conditions to at least 2,500 nucleic acid molecules that encode a Xenorhabdus protein, polypeptide, or fragment thereof.

Nucleic acid molecules of the present invention may be used in site directed mutagenesis. Site-directed mutagenesis may be utilized to modify nucleic acid sequences, particularly as it is a technique that allows one or more of the amino acids encoded by a nucleic acid molecule to be altered (e.g. a threonine to be replaced by a methionine). Any of the nucleic acid molecules of the present invention may either be modified by site-directed mutagenesis or used as, for example, nucleic acid molecules that are used to target other nucleic acid molecules for modification. It is understood that mutants with more than one altered nucleotide can be constructed using techniques that practitioners skilled in the art are familiar with such as isolating restriction fragments and ligating such fragments into an expression vector (see, for example, Sambrook et al., ibid).

Insect inhibitory protein-encoding nucleic acids of the present invention will find particular uses in the plant protection against insects. For instance, insect-resistant transgenic plants can be generated by introducing the exogenous nucleic acids encoding an insect inhibitory polypeptide or protein or insect inhibitory fragment thereof, the amino acid sequence of which is substantially identical to a sequence set forth in SEQ ID NO:7316, SEQ ID NO:9584, SEQ ID NO:9585, SEQ ID NO:9639 and SEQ ID NO:9679. Insect inhibitory protein-encoding nucleic acids of the present invention will also find particular uses in engineering a transgenic microorganism (bacteria or fungi) to express the insect inhibitory polypeptides or proteins of the present invention and then to apply them to the insect food source or allow them to reside in soil surrounding plant roots or on the surface of plant leaves. The transgenic microorganisms of the present invention may be used to produce Xenorhabdus polypeptides or proteins of interest, particularly insect inhibitory polypeptides or proteins. Insect inhibitory polypeptides or proteins or insect inhibitory fragments thereof may be secreted, for example as in bacterial systems, meaning targeted to either the periplasm as for gram negative bacteria or localized to the extracellular space for gram negative or any other type of bacterium, or localized to the intracellular spaces within the cytoplasm.

A principle object of the present invention is to provide a method for identification of any gene or any protein encoded by any structural gene contained within a Xenorhabdus species, particularly those species which are shown to exhibit the production of an insect inhibitory protein or molecule or other similarly active composition, either alone or in combination with proteins or molecules or other similarly active compositions which may be derived from the bacterium in its role as a natural symbiont within an insect pathogenic nematode host. Isolation and identification of a single insect pathogenic nematode species enables the skilled artisan to isolate at least one species of Xenorhabdus endosymbiotic bacteria from the haemolymph of an insect larvae or adult which has been invaded by the isolated and identified host nematode. The isolation and purification of an insect pathogenic nematode Xenorhabdus symbiont bacterium from an insect cadaver provides the basis for obtaining an amount of genomic DNA from which a genomic library can be constructed to represent the entire genome of the bacterial strain. The library can then be manipulated as described herein to produce linear nucleotide sequences, which can then be compared to each other to identify regions of identity with which an overlapping sequence can be generated to produce islands of linear sequence known as contigs because of the contiguous linear sequence assembled from smaller bits of sequence data. The contigs can be assembled into a genomic map from which genes can be identified, and wherein translation of structural genes lead to further identification of proteins having predicted structure and function based on homologies of such predicted protein sequences as translated from open reading frames contained within the genome map, to proteins of known sequence, and perhaps also of known structure and function identified previously from other bacterial, viral, fungal, or other eukaryotic sources.

Xenorhabdus strain Xs85831 and isolatable protein compositions exhibiting insecticidal activity as disclosed herein will find particular utility as insecticides for topical and/or systemic application to field crops, grasses, fruits and vegetables, and ornamental plants. In one embodiment, the bioinsecticide composition comprises an oil flowable suspension of bacterial cells that expresses a novel protein disclosed herein. In another embodiment, the bioinsecticide composition comprises a water dispersible granule. This granule comprises bacterial cells that express a novel insecticidal protein disclosed herein. In a third embodiment, the bioinsecticide composition comprises a wettable powder, dust, pellet, or colloidal concentrate. This powder comprises bacterial cells that express a novel insecticidal protein disclosed herein. Such dry forms of the insecticidal compositions may be formulated to dissolve immediately upon wetting, or alternatively, dissolve in a controlled-release, sustained-release, or other time-dependent manner. In a fourth embodiment, the bioinsecticide composition comprises an aqueous suspension of bacterial cells such as those described above that express the insecticidal protein. Such aqueous suspensions may be provided as a concentrated stock solution which is diluted prior to application, or alternatively, as a diluted solution.

Preferred bacterial cells for fulfilling the above methods may comprise Xenorhabdus Xs85831 cells. However, bacteria such as B. thuringiensis, B. megaterium, B. su, E. coli, Salmonella typhimurium, other Xenorhabdus or Photorhabdus species, or Pseudomonas spp. cells transformed with a DNA segment disclosed herein and expressing the insecticidal protein to are also contemplated to be useful.

Alternatively, the novel Xenorhabdus insecticidal proteins (Xip) of the present invention may be prepared by native or recombinant bacterial expression systems in vitro and isolated for subsequent field application. Such protein may be either in crude cell lysates, suspensions, colloids, etc., or alternatively may be purified, refined, buffered, and/or further processed, before formulating in an active biocidal formulation. Likewise, under certain circumstances, it may be desirable to isolate insecticidal proteins or whole cells from bacterial cultures expressing the insecticidal protein(s) of the present invention and apply solutions, suspensions, or colloidal preparations of such insecticidal proteins or whole cells as the active bioinsecticidal composition.

Regardless of the method of application, the amount of the active component(s) is applied at an insecticidally-effective amount, which will vary depending on such factors as, for example, the specific coleopteran insects to be controlled, or the specific piercing and sucking insect to be controlled, the specific plant or crop to be treated, the environmental conditions, and the method, rate, and quantity of application of the insecticidally-active composition.

The insecticide compositions described herein may be made by formulating either the bacterial cells, insecticidal protein suspensions, or isolated protein components with the desired agriculturally acceptable carrier (U.S. Pat. No. 6,177,615). The compositions may be formulated prior to administration in an appropriate means such as lyophilized, freeze-dried, desiccated, or in an aqueous carrier, medium or suitable diluent, such as saline or other buffer. The formulated compositions may be in the form of a dust or granular material, or a suspension in oil (vegetable or mineral), or water or oil/water emulsions, or as a wettable powder, or in combination with any other carrier material suitable for agricultural application (U.S. Pat. Nos. 5,616,319 and 5,942,658). Suitable agricultural carriers can be solid or liquid and are well known in the art. The insecticidal compositions of this invention are applied to the environment of the target coleopteran or piercing and sucking insect, typically onto the foliage of the plant or crop to be protected, by conventional methods, preferably by spraying (U.S. Pat. No. 6,177,615). The strength and duration of insecticidal application will be set with regard to conditions specific to the particular pest(s), crop(s) to be treated and particular environmental conditions. The proportional ratio of active ingredient to carrier will naturally depend on the chemical nature, solubility, and stability of the insecticidal composition, as well as the particular formulation contemplated.

Other application techniques, e.g., dusting, sprinkling, soaking, soil injection, seed coating, seedling coating, spraying, aerating, misting, atomizing, and the like, are also feasible and may be required under certain circumstances such as e.g., insects that cause root or stalk infestation, or for application to delicate vegetation or ornamental plants. These application procedures are also well known to those of skill in the art.

The insecticidal composition of the invention may be employed in the method of the invention singly or in combination with other compounds, including and not limited to other pesticides. The method of the invention may also be used in conjunction with other treatments such as surfactants, detergents, polymers or time-release formulations. The insecticidal compositions of the present invention may be formulated for either systemic or topical use.

Having now generally described the invention, the same will be more readily understood through reference to the following examples that are provided by way of illustration, and are not intended to be limiting of the present invention, unless specified.

EXAMPLES

Example 1

This example illustrates the isolation and characterization of a *Steinernema* race of nematode that contains a *Xenorhabdus* bacterium, strain Xs8583.

The *Xenorhabdus* bacterium, strain Xs85831, was isolated from entomopathogenic *Steinernema* nematodes according to the following procedure. Entomopathogenic nematodes were isolated from soil samples obtained from various geographic locations and entomopathogenic nematode suspensions were prepared according to the entomopathogenic nematode baiting method as disclosed in the US patent application (application Ser. No. 09/897,516). A variety of fourth instar insect larvae that included corn ear worm, tobacco bud worm, black cut worm, beet army worm, boll weevil, western corn rootworm and *Galleria mellonella* were placed individually in a 24-well plate containing Whatman filters in each well. Approximately ten microliters (µL) of an entomopathogenic nematode suspension were added into each well with one insect. The plates was sealed with Parafilm™ and placed at 25° C. in the dark.

After 48 to 72 hours dead insect larvae were removed from the 24 well plate. The insect larvae were surface sterilized [20 milliliter (mL) $H_2O$, 3 mL 4M NaOH and 1 mL 5% NaOCl] for 5 minutes and air-dried. The insect larvae were cut open with sterile instruments on the lateral side without injuring the gut and the hemolymph was streaked on indicator plates (nitro blue tetrazolium agar plates containing nutrient agar). The agar plates were incubated at 30° C. in the dark for 48 hours.

Characteristic blue colonies were selected from the indicator plates: phase I *Xenorhabdus* bacteria are able to take up bromthymol blue dye from the NBT agar and form the blue colonies. Bacterial characterization was performed according to methods known to the one skilled in the art (Farmer, *Bergey's Manual of Systematic Bacteriology, Vol.* 1: 510-511, 1984; Akhurst & Boemare, *J. Gen. Microbiol., Vol.* 133: 1835-1845, 1988; Boemare et al., *Int. J. Syst. Bacteriol., Vol.* 44: 249-255, 1993).

Single characteristic phase I colonies were picked up by an inoculation loop and suspended into BHI media (Brain Heart Infusion medium (Difco), 32 g/l, 50 mL in a 250 mL baffled flask). The bacteria were grown at 25° C. at 280 rpm on a rotary shaker in the dark. After 24 hours 15% glycerol was added to the bacterial culture, 1.5 mL aliquots for stock cultures were placed into cryovials and stored at −80° C.

The isolated *Xenorhabdus* strain Xs85831 was deposited according to the Budapest Treaty on the International Recognition of the Deposit of Microorganisms for the Purpose of Patent Procedures with the Agriculture Research Culture Collection (NRRL) International Depositary Authority at 1815 North University Street, in Peoria, Ill., ZIP 61604, U.S.A., on Jun. 28, 2000 and designated as NRRL-30311. It is contemplated for use as a source for DNA sequences encoding insecticidal and other types of useful proteins, and when formulated into a composition of matter as a spray, powder or emulsion, for the treatment of plants or animals to inhibit insect infestation and the like.

Example 2

This example illustrates the construction of genomic DNA libraries from *Xenorhabdus* strain Xs85831 genomic DNA.

Genomic DNA from *Xenorhabdus* strain Xs85831 was prepared for constructions of genomic libraries using methods well known in the art. Xs85831 bacterial cells were grown in brain heart infusion broth (Difco) for 42 hours at 25° C. to mid-exponential phase (OD650=~1.0). Cells were poured into ten 1.5 mL-microcentrifuge tubes and spun for 5 minutes at ~10,000 RPM to pellet. The supernatant was removed and the cells were frozen. The frozen pellets were resuspended into 200 µL of TE (10 mM Tris, 1 mM EDTA, pH 8.0). Genomic DNA was prepared from the frozen cell pellets using the Promega Genomic Preparation kit following the instructions of the manufacturer (Madison, Wis.). Ten DNA samples were prepared from the cells above, and two of the samples were resuspended into 50 µL of TE. Sample purity was tested and confirmed by digestion using the restriction enzymes EcoRI, HindIII, NotI, and SalI. The resuspended samples were used for the preparation of a genomic library.

The genomic libraries of *Xenorhabdus* strain Xs85831, for example, LIB4151 and LIB4152, were prepared according to standard procedures well known to those skilled in the art. Genomic DNA was sheared and then polished with T4 polymerase and T4 polynucleotide kinase. LIB4151 was constructed from fragments 1.6-2.5 kb in length, while LIB 4152 was constructed from fragments 2.5-3.5 kb in length. Size fractionated fragments were recovered from an agarose gel. Blunt end ligation was used to clone DNA fractions into the Sma I site of the standard cloning vector pUC18. The resulting ligation reactions were transformed into *E. coli* DH10B. The resulting vector fragment contains an intact beta-lactamase coding sequence enabling selection of transformed cells containing genomic DNA insertions on media containing ampicillin. Several ampicillin resistant transformants were selected and streaked in duplicate onto media containing ampicillin to determine the efficiency of the library construction. 80% of colonies arising from the transformation contained an insert, presumably derived from the genomic sequences. Approximately 150,000 colony-forming units per microliter of ligation mix were obtained. About thirty thousand individual recombinant colonies from each library were selected for DNA sequence analysis of inserted genomic DNA.

Example 3

This example illustrates the generation of contiguous nucleotide sequences from the sequencing information generated from the library clones prepared in Example 2.

About 74,000 genomic nucleotide sequence traces were derived from the double stranded plasmid library as described in Example 2. The two basic methods for the DNA sequencing are the chain termination method of Sanger et al., *Proc. Natl. Acad. Sci.* (*U.S.A.*) 74:5463-5467, 1977) and the chemical degradation method of Maxam and Gilbert, *Proc. Natl. Acad. Sci.* (*U.S.A.*) 74:560-564, 1977). PHRED (phragment editor, Phil Green, University of Washington) was used to call the bases from the sequence trace files and to assign quality scores to the bases. After the base calling is completed, sequence preprocessing is performed by removing 5' and 3' vector and linker sequences, according to standard procedures well known in the art. The preprocessed sequences were then assembled into contigs, or groups of overlapping sequences. Contigs are assembled using PHRAP (phragment assembly program, Phil Green, University of Washington) using default assembly parameters.

A total of 444 contigs were obtained and contig sequences were recognized as those sequences whose designations begin with the letter designation "Xb4151_4152.C". All contig sequences were run through the annotation and gene selection processes as described in Examples 4 and 5 below. The contig sequences are listed in the Sequence Listing file from SEQ ID NO:14542 to SEQ ID NO:14985.

Example 4

This example illustrates the identification of different coding sequences, open reading frames, and the like within the 444 contigs assembled as described in Example 3.

The genes, open reading frames, other predicted expressed sequences, and partial genes embedded in the contiguous (CONTIG) sequences were identified through a series of informatics analyses. Homology-based searches (i.e., BLASTX) were used to detect conserved sequences during comparisons of DNA sequences or hypothetically translated protein sequences to public and/or proprietary DNA and protein databases. Novel genes, i.e., with no known homologs, were predicted with the program GeneMark provided by Borodovsky's Bioinformatics Group at the Georgia Institute of Technology, Atlanta, Ga. The results of the homology and predictive methods were then merged into a single set of predicted coding regions, and their most probable translation.

The homology-based method used to define the *Xenorhabdus* gene set was BLASTX (see Coulson, *Trends in Biotechnology* 12:76-80, 1994; Birren et al., *Genome Analysis*, 1:543-559, 1997). BLASTX takes a nucleotide sequence, translates it in three forward reading frames and three reverse complement reading frames, and then compares the six translations against a protein sequence database (e.g. the non-redundant protein (i.e., nr-aa) database at NCBI). BLASTX is run with the *Xenorhabdus* contigs as queries against the GenBank non-redundant protein data library. To identify genes solely by BLASTX, the maximum BLASTX E value is set at 1E-08.

The method used to define the *Xenorhabdus* gene set was GeneMark. Protein-encoding regions in the *Xenorhabdus* nucleic acid molecules of the present invention were identified and the BLAST results and GeneMark analyses are provided in the Sequence Listing feature fields.

Example 5

This example illustrates the identification of peptides, tRNA, rRNA, promoter sequences, translational termination sequences, and the like from bioinformations analyses of the derived sequences.

The *X. bovienii* genome from strain Xs85831, as assembled from LIB4151 and LIB4152, consisted of $4.5 \times 10^6$ bases from the 444 sequence contigs. The smallest contig sequence had 126 bases and the largest one had 524707 bases, with an average contig size of 10,610 base pairs. The sequence contigs were annotated to identify genes and gene regulation elements. As a result, 5313 protein-coding genes (SEQ ID NO:1 through SEQ ID NO:5313, 2388 promoters (SEQ ID NO:10627 through SEQ ID NO:13014), 1436 terminators (SEQ ID NO:13015 through SEQ ID NO:14450), 19 ribosomal RNA genes (SEQ ID NO:114451 through SEQ ID NO:14469) and 72 transfer RNA genes (SEQ ID NO:14470 through SEQ ID NO:14541) were identified.

The *Xenorhabdus* genome was annotated by searching for homology to genes of known functions. These searches were done using homology to whole protein using BLAST as well as similarity to protein domains using Pfam and Hidden Markov Model algorithms. The annotations were then associated with the ORFs predicted by protein prediction models. The genome annotation was completed with FGENESB (Softberry, Inc., Mount Kisco, N.Y.), a bacterial gene/operon prediction and annotation pipeline developed by Softberry Inc. (Mount Kisco, N.Y., USA). The annotation database and parameters were updated and customized when processing *X. bovienii* genome. These annotations were assembled into a database that could be queried by searching for key words using wildcard text searches.

The analysis was done by performing keyword searches against the annotated genome sequences in the database. The present inventors contemplate that, since *Xenorhabdus* is an insect pathogen of, it may contain potent insecticidal molecules that are similar to the toxin complex (tc) toxins previously shown to be associated with *Photorhabdus*. The present inventors further contemplate that there may be many genes that are associated with virulence and pathogenesis in other eukaryotes. These may include, for example, hemolysins, lipases, and RTX (repeats in toxin) family of cytolytic toxins. All *Xenorhabdus* genes encoding proteins that exhibited homology to those proteins found in *Drosophila* (Fruit Fly) or *Anopheles* (mosquitos) were searched for homology to genes of known functions, as those genes may be those that affect pathogenesis in insects. Homologs of fungicides, nematocides, and other microcides, histone, proteins sequestering iron, polyketides and Non-ribosomal (NRP) peptides and HrpA-helicase were also searched for homology to genes of known functions. In addition, possible nematocides were searched using the prefix "Nema*", where the symbol "*" equals to a wild card. The exemplary key words used to conduct the searches included tc, toxin, RTX, hemolysin, lipase, chitinase, protease, ferritin, iron, chelin, arsenite, toluene, resistance, colicin, restriction, *Anopheles*, insect, *Drosophila*, ketide, NRP, polyketides, non-ribosomal, polymer, nema and nematode. A wild card was used with all searches.

The search results have shown that the *Xenorhabdus* strain Xs85831 has proteins that are homologous to many important known proteins or polypeptides. The search for homologs has also led to some new discoveries. Discovery of histone homologs was new as histones were not previously found in bacteria. These genes might make histones that would affect an insect's growth and development by disrupting its normal cellular processes. Fungicides and nematocides fell into many classes. The first step was done to look for any annotation containing the word "resistance" and put them into first class. Often these homologs referred to resistance to metals (e.g. tellurite resistance) or antibiotics (e.g. tetracycline resistance). Resistance homologs may also came about from small phage-like particles called colicins. These proteins may often be evolved from phage tails. Polyketides and non-ribosomal (NRP) peptides were very large proteins, often greater than 1000 amino acid residues, for example, SEQ ID NO's: 6035, 6037 and 8093). Proteins that affected fungi and insect skeletons included chitinases. Proteins sequestering iron were often a virulence determinant. Homologs identified included chelin and ferritin. HrpA-helicase homologs may be involved in a plant's DNA metabolism and may be used to improve plant transformation.

In summary, the nucleotide sequences are identified herein that encode many useful *Xenorhabdus* polypeptides or proteins, including but not limited to insect inhibitory polypeptides or proteins as set forth in SEQ ID NO's 7316, 9584, 9585, 9639 and 9679; cytotoxin proteins as set forth in SEQ ID NO's 5524, 5845, 5846, 5901, 5932, 5975, 6700, 7023, 7373, 7374, 7375, 7377, 7563, 7877, 8566, 8624, 8632, 8721, 8735, 9429, 9628, 9704, 9738, 9774, 9777, 9779, 9833, 10005, 10322, 10368, 10598 and 10605, which may be used as microbial inhibitory proteins including bactericidal, bacteriostatic, fungicidal, and fungistatic polypeptides or proteins; polyketide synthases as set forth in SEQ ID NO's 6034, 6035, 6037, 6038, 6040, 6041, 6042, 6817, 7170, 7360, 7361, 7362, 7363, 7550, 8093, 8094, 8095, 8186, 8686, 8687, 9049, 9100, 9101, 9104, 9108, 9322, 9324, 10039, 10228, 10229, 10257 and 10258; proteases as set forth in SEQ ID NO's 5589, 5625, 5958, 5959, 6156, 6298, 6300, 6404, 6530, 6602, 6839, 7599, 7682, 7706, 7735, 7737, 7941, 7999, 8072, 8137, 8267, 8568, 9284, 9336, 9368, 9729, 9921, 9984, 10021, 10022, 10143, 10201, 10263, 10327, 10371, 10372, 10411, 10412, 10413, 10430, 10580 and 10582; chitinases as set forth in SEQ ID NO's 6895, 8218, 8222, 10427 and 10583; restriction enzymes as set forth in SEQ ID NO's 6835, 7488, 8128, 8129, 8132, 8901, 8902, 8903 and 9854; histone homologues as set forth in SEQ ID NO's 5672, 5923, 6188, 7790, 7816, 7835, 8060, 9246, 9672, 9907, 9916, 10115, 10199, 10517 and 10540; ferritin homologues as set forth in SEQ ID NO's 5769, 5770, 6289 and 7552; biopolymer transport proteins as set forth in SEQ ID NO's 5799, 5801, 5802, 10481 and 10482; polypeptides or proteins capable of conferring resistance to heavy metals or other toxic compositions as set forth in SEQ ID NO's 6291, 6521, 7064, 7069, 7726, 7727, 7729, 7962, 8108, 8284, 10189, 10190, 10326 and 10406; Hrp-like helicase homologues as set forth in SEQ ID NO:8465 and SEQ ID NO:10227; and protein homologues to proteins from *Anopheles* species as set forth in SEQ ID NO:9502 and SEQ ID NO:9512. These proteins or polypeptides, offered by way of illustration and not by way of limitation, are just some of the exemplary proteins or peptides from the *Xenorhabdus* strain Xs85831 that are homologous to known proteins or polypeptides. Predictive functions and utilities of these exemplary proteins or peptides are described in the feature fields as set forth in the Sequence Listing.

Example 6

This example illustrates the evaluation of insecticidal proteins produced by *Xenorhabdus* strain Xs85831.

Insect inhibitory proteins produced by *Xenorhabdus* strain Xs85831 were evaluated using the following procedure. A 250 mL baffled flask containing 50 mL BHI medium in was inoculated with 1.5 mL bacterial stock culture and incubated at 25° C. and 280 rpm on a rotary shaker in the dark for 48 hours. The culture was frozen at −80° C. for at least 24 hours. The culture broth was then thawed, centrifuged at 2600×g for 30 minutes at 4° C. and decanted from the cell and debris pellet. The broth was then sterile-filtered (0.2 μm) and dialyzed. The culture supernatant was used without an additional concentration step for bioassays to evaluate insect inhibitory, fungicidal and bactericidal properties. Larvae were obtained using insect eggs obtained from commercial sources, hatched and reared using conventional methods.

Insect inhibitory activity was evaluated against members of the insects in the order Coleoptera that included Western corn rootworm (WCR, *Diabrotica virgifera virgifera*), Southern corn rootworm (SCR, *Diabrotica undecempunctata howardi*) and cotton boll weevil (BWV, *Anthomonas grandis grandis*). Insect inhibitory activity against corn rootworm larvae was evaluated as follows. *Xenorhabdus* culture supernatant, control medium (BHI) or Tris buffer, pH 7.0, was applied to the surface (about 0.38 cm$^2$) of a modified artificial diet (Bioserv™; diet product F9757) in 20 μL aliquots. The plates were allowed to air-dry in a drying chamber (16-20° C.; 40-50% RH) and the wells were infested with single non-diapausing neonate WCR hatched from surface disinfested eggs (Pleau, Master of Science Thesis, Saint Louis University, 1999). Plates were sealed, placed in a humidified growth chamber and maintained at 27° C. for the appropriate period (5-7 days). Mortality and stunting (0-3) scores were then assessed and statistically analyzed (SAS institute, user's manual for JMP version 3.2, 1989-1997). Twenty-four insects per treatment were used in all studies. Control mortality was generally less than 10%.

Insect inhibitory activity against the cotton boll weevil was evaluated as follows. *Xenorhabdus* supernatant, control medium (BHI) or Tris, pH 7.0, were applied in 20 μL aliquots to the surface of 200 μL of artificial diet (Bioserv™ Co., Frenchtown, N.J.; diet product F9247) and allowed to air-dry. Boll weevil eggs were then placed into the wells, the wells sealed and the plates held at 27° C., 60% relative humidity (RH) for 6 days. An activity score, based on confounding of frass production, growth and mortality was then assessed and analyzed statistically (SAS institute, ibid). Control mortality ranged between 0% and 25%.

The bacterial culture supernatant exhibited activity against Lepidopteran larvae, such as the tobacco budworm (TBW, *Heliothis virescens*), cotton bollworm (CBW, *Heliothis zea*), corn earworm (CEW, *Helicoverpa zea*), beet armyworm (BAW, *Spodotera exigua*), and black cutworm (BCW, *Agrotis ipsylon*). Activity was also observed against the European corn borer (ECB, *Ostrinia nubilalis*).

Insect inhibitory activity against Lepidopteran larvae was tested as follows. *Xenorhabdus* culture supernatant, control medium (BHI) and Tris buffer, pH 7.0, were applied directly to the surface (about 0.38 cm$^2$) of standard artificial Lepidopteran diet (Southland Products Incorporated, Lake Village, Ark.; Lepidopteran multi-species diet) in 20 µL aliquots. The diet plates were allowed to air-dry in a drying chamber (16-20° C.; 40-50% RH). The test wells were then infested with insect eggs of TBW, CEW or BCW suspended in agar. In the case of ECB, neonates were hand infested into the wells at one neonate per well. Following infestation, diet plates were sealed, placed in a humidity controlled growth chamber and maintained in the dark at 27° C. for the appropriate period of time. Mortality and stunting measurements were scored at day 5 and statistically analyzed (SAS institute, 1989-1997, User's manual for JMP version 3.2). Generally 24 insects per treatment were used in all studies. Control mortality generally ranged from 0-12.5%.

Insect inhibitory activity was also tested against *Lygus* bugs (Western Tarnished Plant Bug (WTPB), *Lygus hesperus* Knight) in the order Hemiptera. The insect inhibitory activity against *Lygus* bug was tested as follows. Feeding domes were made using a dome-making machine manufactured by Analytical Research Systems (Gainesville, Fla.). Briefly, the system used a vacuum to form domes from Parafilm™ sheeting using an aluminum block template shaped in the form of a 96-well microtiter-plate. To each such formed dome was added 40 uL of a 1:10 (v/v) dilution of test solution in diet. The dome-molded Parafilm™ was then heat sealed with a sheet of Mylar. The resulting Parafilm™ dome sheet (96-wells) was placed onto a 96-well flat-bottomed microtiter plate containing one *Lygus* nymph per well. The assay was typically scored after 4 days for mortality and stunting, using a scale of 0 (no mortality or stunting) to 3 (complete mortality).

The bioassay results demonstrated that the culture supernatant containing insecticidal proteins from *Xenorhabdus bovienii* strain Xs85831 exhibited significant insecticidal activity against most of the insect species tested. Specifically, the culture supernatant exhibited very strong insecticidal activity against BCW, CEW, SCR and TBW and exhibited a comparatively weak insecticidal activity against WCR and FAW. However, the bioassays conducted have not yet shown that the culture supernatant exhibited any insecticidal activity against BWV and WTPB.

Example 7

This example illustrates the construction of a plant transformed to express a protein of the present invention.

It is desirable to express a XIP protein such as that set forth in SEQ ID NO:7316 (a *Photorhabdus* species TcaC insecticidal protein homologous sequence) in a cotton plant to protect cotton plants from *lygus* bug infestation. A nucleotide sequence preferred for expression in a cotton plant, or other dicot plant, is constructed according to the method of U.S. Pat. No. 5,500,365 to achieve a sequence that exhibits improved levels of expression of the TcaC homologous amino acid sequence in cotton plants. The synthetic nucleotide sequence encoding the TcaC related amino acid sequence is introduced into a plant expression cassette in a plant expression vector under the control of a plant functional promoter, and the expression cassette is introduced into the cotton cells along with a selectable marker. Cotton plants (transgenic events) are produced after an appropriate period of time that contain the expression cassette with the synthetic XIP expression sequence. Transgenic cotton events are screened for expression of the TcaC homologous protein using antibodies specific for the TcaC homologous protein. Transgenic events exhibiting preferred levels of expression of the TcaC homologous protein are exposed to *lygus* bug infestation and control of *lygus* infestation is scored, and events that exhibit the greatest levels of control become commercially acceptable commercial embodiments.

In summary, the above specification describes preferred embodiments of the present invention. It will be understood by those skilled in the art that, without departing from the scope and spirit of the present invention and without undue experimentation, the present invention can be performed within a wide range of equivalent parameters. While the present invention has been described in connection with specific embodiments thereof, it will be understood that it is capable of further modifications. The present invention is intended to cover any uses, variations, or adaptations of the invention following the principles of the invention in general. Various permutations and combination of the elements provided in all the claims that follow are possible and fall within the scope of this invention.

SEQ ID NO's referred to herein are listed in the Sequence Listing on CD-ROM which accompanies this specification, and are not provided in paper copy due to the large number of pages that would be required for handling of the sequence listing.

All patent publications referred to in this specification are incorporated herein by reference.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US07629444B1). An electronic copy of the "Sequence Listing" will also be available from the USPTO upon request and payment of the fee set forth in 37 CFR 1.19(b)(3).

What is claimed is:

1. An isolated polynucleotide encoding a *Xenorhabdus* strain Xs85831 protein, wherein said protein comprises the amino acid sequence as set forth in SEQ ID NO:7316.

2. The isolated polynucleotide of claim 1, comprising the nucleotide sequence as set forth in SEQ ID NO:2003.

3. An isolated polynucleotide of claim 2, wherein said *Xenorhabdus* strain Xs85831 has an Agriculture Research Culture Collection (NRRL) deposit number 30311.

4. An isolated polynucleotide encoding a *Xenorhabdus* strain Xs85831 protein, wherein said protein is at least 95% identical to the amino acid sequence set forth in SEQ ID NO:7316, and exhibits insecticidal activity.

5. The isolated polynucleotide encoding a *Xenorhabdus* strain Xs85831 protein of claim 4, wherein said protein is at least 99% identical to the amino acid sequence set forth in SEQ ID NO:7316, and exhibits insecticidal activity.

6. The isolated polynucleotide encoding a *Xenorhabdus* strain Xs85831 protein of claim 4, wherein said protein is at least 98% identical to the amino acid sequence set forth in SEQ ID NO:7316, and exhibits insecticidal activity.

* * * * *